United States Patent [19]
Bonutti

[11] Patent Number: 5,685,830
[45] Date of Patent: Nov. 11, 1997

[54] ADJUSTABLE ORTHOSIS HAVING ONE-PIECE CONNECTOR SECTION FOR FLEXING

[76] Inventor: Peter M. Bonutti, 1303 W. Evergreen Plaza, Effingham, Ill. 62401

[21] Appl. No.: 488,194

[22] Filed: Jun. 7, 1995

Related U.S. Application Data

[60] Continuation-in-part of Ser. No. 293,035, Aug. 19, 1994, Pat. No. 5,456,268, which is a division of Ser. No. 978,103, Nov. 18, 1992, Pat. No. 5,365,947, which is a division of Ser. No. 559,700, Jul. 30, 1990, Pat. No. 5,167,612.

[51] Int. Cl.$^6$ ........................................ A61F 5/00
[52] U.S. Cl. ........................ 602/16; 602/20; 602/23; 602/36; 602/37; 601/33
[58] Field of Search ..................... 602/5, 16, 20, 602/23, 36, 37; 601/23, 33, 34, 40

[56] References Cited

U.S. PATENT DOCUMENTS

| | | |
|---|---|---|
| 432,327 | 7/1890 | Beacock. |
| 2,237,252 | 4/1941 | Longfellow ................ 602/20 |
| 3,698,389 | 10/1972 | Guedel ...................... 602/20 |
| 3,814,419 | 6/1974 | Bjorklund et al.. |
| 4,039,183 | 8/1977 | Sakurada. |
| 4,180,870 | 1/1980 | Radulovic et al.. |
| 4,237,873 | 12/1980 | Terry et al.. |
| 4,363,481 | 12/1982 | Erickson. |
| 4,441,489 | 4/1984 | Evans et al.. |
| 4,456,002 | 6/1984 | Barber et al.. |
| 4,508,111 | 4/1985 | Hepburn. |
| 4,538,600 | 9/1985 | Hepburn. |
| 4,612,919 | 9/1986 | Best. |
| 4,665,905 | 5/1987 | Brown. |
| 4,790,301 | 12/1988 | Silfverskiold. |
| 4,844,454 | 7/1989 | Rogers. |
| 4,848,326 | 7/1989 | Lonardo. |
| 4,930,497 | 6/1990 | Saringer. |
| 4,955,369 | 9/1990 | Bledsoe et al.. |

FOREIGN PATENT DOCUMENTS

| | | |
|---|---|---|
| 0181688 | 9/1985 | European Pat. Off.. |
| 2829562 | 1/1980 | Germany. |
| 8062317 | 5/1988 | Germany. |
| 1426580 | 9/1988 | U.S.S.R.. |
| 8804543 | 12/1986 | WIPO. |

*Primary Examiner*—Linda C. Dvorak
*Attorney, Agent, or Firm*—Tarolli, Sundheim, Covell Tummino & Szabo

[57] ABSTRACT

An adjustable orthosis for stretching tissue by moving a joint between first and second relatively pivotal body portions. The orthosis includes a first arm with a cuff at its outer end to releasably attach the first arm to the first body portion. A second arm with a cuff at its outer end releasably attaches the second arm to the second body portion. The arms are pivotally interconnected by a connector section which is formed as one-piece with the first and second arms. An actuator is connected to the arms to apply force to the arms to pivot them relative to each other to move the joint. The actuator includes flexible force transmitting member connected with at least one of the arms. A drive assembly is provided to tension the flexible force transmitting member and move the first and second arms relative to each other.

136 Claims, 12 Drawing Sheets

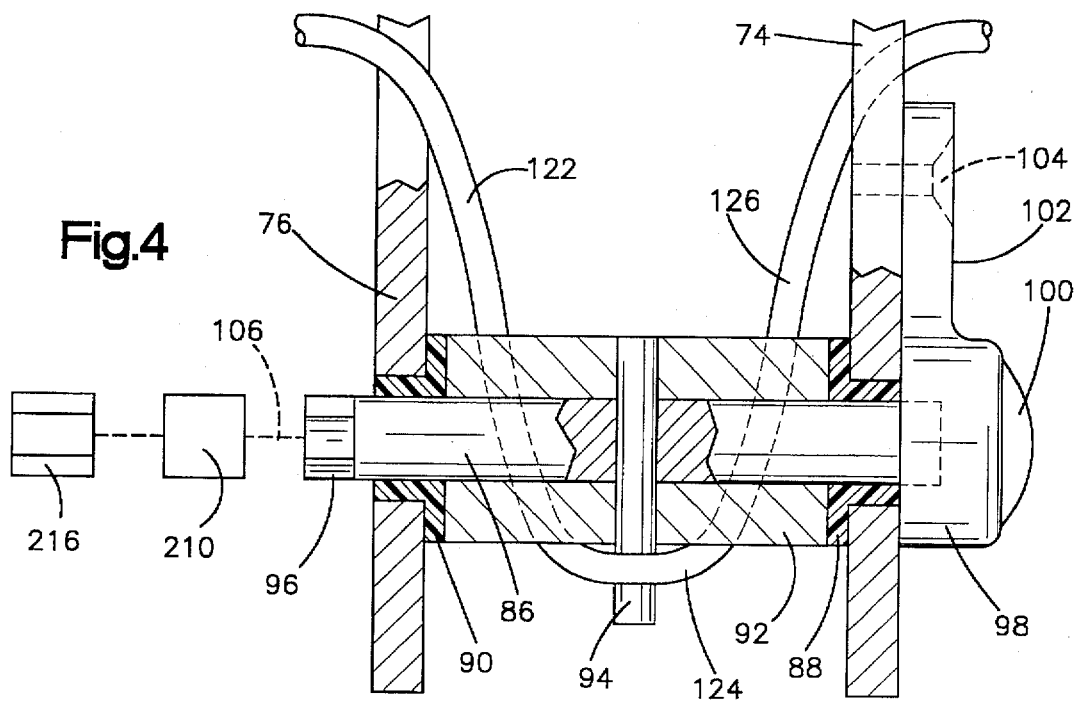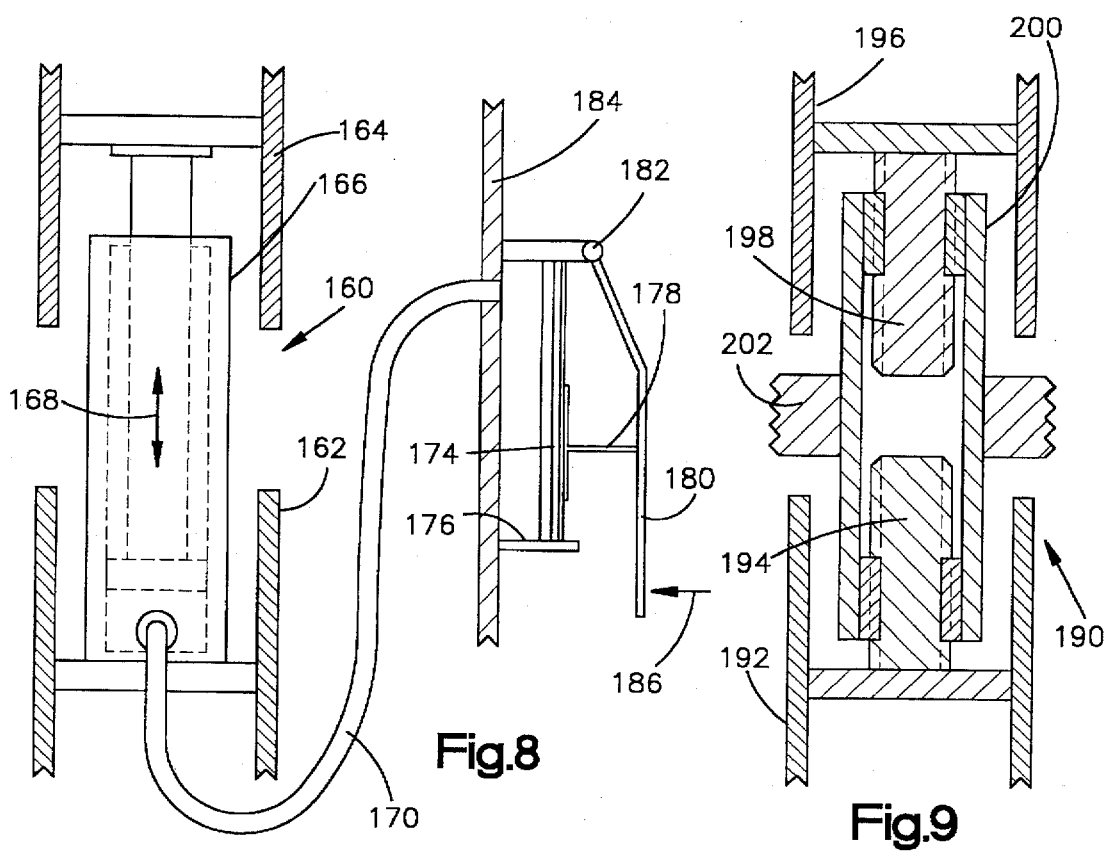

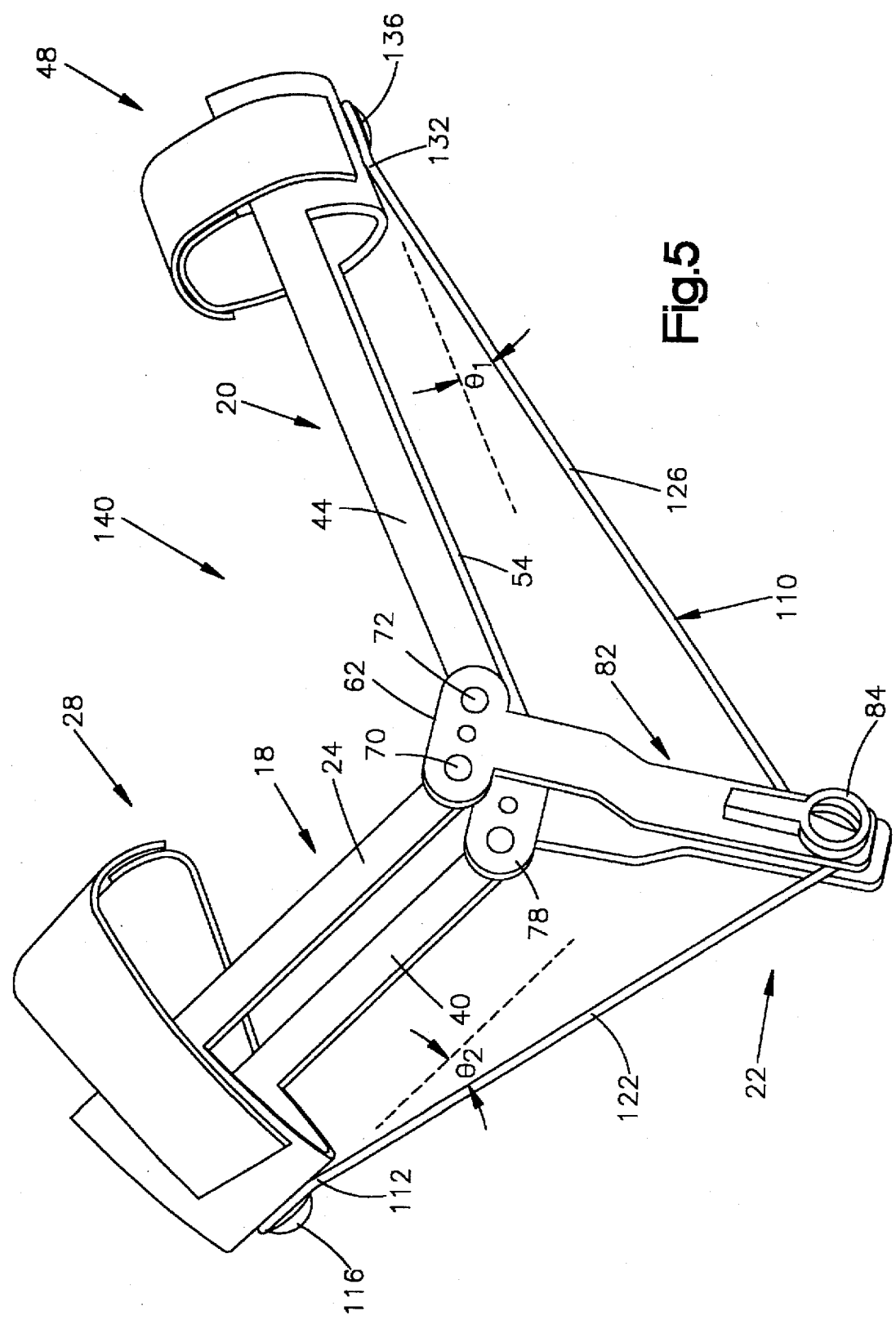

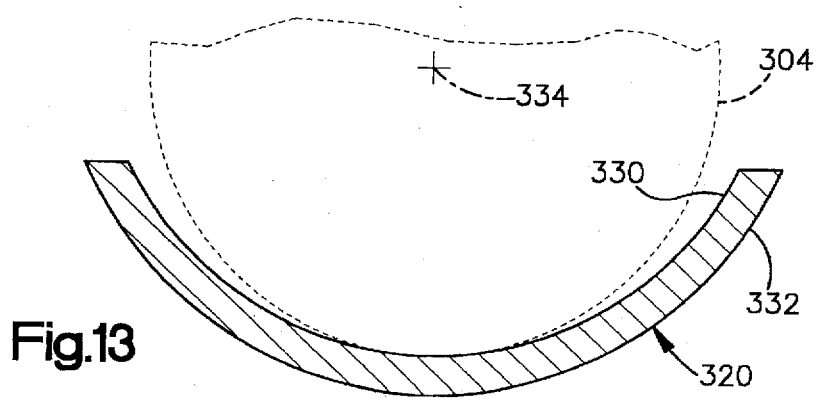
Fig.13
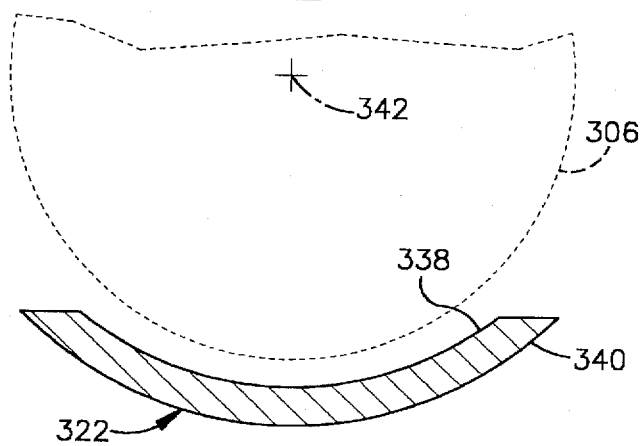
Fig.14
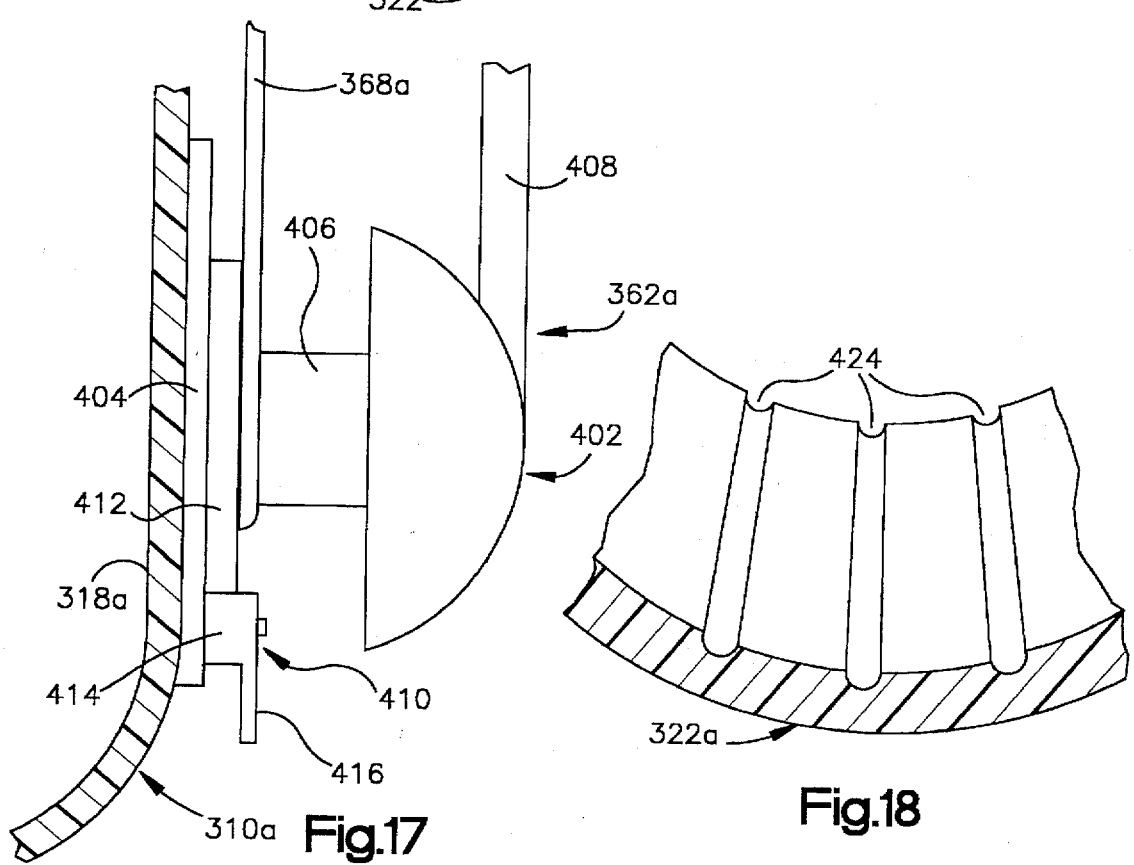
Fig.17
Fig.18

ADJUSTABLE ORTHOSIS HAVING ONE-PIECE CONNECTOR SECTION FOR FLEXING

RELATED APPLICATIONS

This application is a continuation-in-part of U.S. patent application Ser. No. 08/293,035 filed Aug. 19, 1994 (now U.S. Pat. No. 5,456,268). The aforesaid application Ser. No. 08/293,035 is itself a divisional of U.S. patent application Ser. No. 07/978,103 filed Nov. 18, 1992 (now U.S. Pat. No. 5,365,947). The aforesaid application Ser. No. 07/978,103 is itself a divisional of U.S. patent application Ser. No. 07/559,700 filed Jul. 30, 1990 (now U.S. Pat. No. 5,167,612).

BACKGROUND OF THE INVENTION

1. Technical Field

The present invention relates to an adjustable orthosis for stretching tissue in the human body. In particular, the present invention relates to an adjustable orthosis which can be used for stretching tissue such as ligaments, tendons or muscles around any joint during flexion or extension of the joint.

2. Description of the Prior Art

Best U.S. Pat. No. 4,612,919 shows an adjustable limb support for adjustably orienting the forearm and upper arm of a human patient in a variety of angular relationships to therapeutically treat the contracted muscles in the patient's arm.

Lonardo U.S. Pat. No. 4,848,326 shows a knee contracture correction device for straightening a contracted knee. The device includes a pair of rod assemblies each having opposite upper and lower ends and a pivotal joint between the ends. The upper end of the rod assemblies is pivotally secured to the patient's thigh while the lower end is pivotally secured adjacent the patient's ankle. The pivotal joint of the rod assemblies is locked so as to define an obtuse angle slightly greater than the angle of contracture of the knee. Straps are then positioned immediately above and below the knee and fastened to the rod assemblies so as to stretch the knee ligaments and muscles. Periodically, the angle of the rod assemblies is increased until eventually the knee contracture is eliminated.

Hepburn U.S. Pat. No. 4,538,600 shows an adjustable splint assembly with a lower strut and an upper strut pivotably connected to the lower strut. An internal spring applies a force at the pivot point to align the upper and lower struts to straighten the limb to which the splint is attached. A similar device is also shown in Hepburn U.S. Pat. No. 4,508,111. Similar devices are in use and are sold under the trademark DYNASPLINT by Dynasplint Systems, Inc.

Rogers U.S. Pat. No. 4,844,454 shows a portable, manually operable knee exerciser having a handle grasped by the user to pivot the lower leg relative to the upper leg.

Brown U.S. Pat. No. 4,665,905 shows a dynamic elbow and knee extension device with a centrally positioned compression spring.

It is also known in the art to put a rigid element including a turnbuckle, on the inside angle of a joint, between two cuffs attached to limb segments and use the turnbuckle to vary the length of the rigid element to pull and push the limb segments relative to each other. It has been found that this device does not work very well in practice because it is cumbersome and difficult to obtain relatively full extension at the extreme of motion.

SUMMARY OF THE INVENTION

The present invention is an adjustable orthosis for moving a joint between first and second relatively pivotable body portions. The joint and the first and second body portions define on one side (the flexor side) of the joint an inner sector which decreases in angle as the joint is flexed (bent) and on the opposite side (the extensor side) of the joint an outer sector which decreases in angle as the joint is extended (straightened). The orthosis includes a first arm or section, first cuff means on the first arm for releasably attaching the first arm to the first body portion, a second arm or section, and second cuff means on the second arm for releasably attaching the second arm to the second body portion. The first and second arms are connected with each other intermediate the first and second cuff means. An actuator means is connected to the first and second arms for applying force to the first and second arms to pivot the first and second arms relative to each other to move the joint. The actuator means may include flexible force transmitting means connected with at least one of the arms, and drive means for applying force to the flexible force transmitting means to move the first and second arms relative to each other. The drive means may be supported in the outer sector at a distance from the pivotal connection of the arms substantial enough to ensure a significant mechanical advantage. Of course, many different actuator means may be used.

Tissue is viscoelastic. It will stretch, then return to (or almost to) its original state, but will have acquired a greater range of motion by having been stretched. Tissue requires intermittent forceful stretching to improve the range of motion. The key to good stretching is therefore graduated, progressive stressing (stretching) of the tissues at the joint. One avoids tissue damage by such gradual progressive modulated stretching of the tissue (stress relaxation of tissue). Gradual stretching does not damage tissues, as a sudden force would.

In therapy, one must first develop a range of motion before strengthening the muscles. The most difficult area is to work on the extremes of motion. A patient can't feasibly go to a therapist three times a day. The present invention provides an orthosis which a patient can use at home, by himself, without a therapist. The orthosis can be used up to several times a day so as not to lose, by long periods of inaction, the benefits gained from each stretching session. Since the patient is awake, he can modulate the force applied, preventing damage by stopping when it is too painful.

With the frequent use of this device, the tissues will progressively stretch out, for an improved range of motion. The patient can tighten the tissues, wait a few minutes, then tighten some more, progressively, using the stress relaxation ability of tissue. This also is practically not feasible with a therapist.

The flexible force transmitting means is, in one embodiment of the invention, preferably a rope or cable. Although a winch and rope are disclosed herein as the preferred drive means, any structure which controllably and progressively tightens a rope or cable or chain etc. can be used, not just a winch. The winch is the simplest, and has an releasable ratchet drive which prevents the orthosis from returning to a previous position after it is tightened to a certain degree.

The orthosis of the present invention also has a fine range of control with the winch for tension adjustment. The winch provides easily controllable and repeatable, graduated force.

It is desirable to stretch tissue without increasing the joint reactive force. Pulling apart a joint is mechanically advantageous to pushing it apart. There is less joint reactive force with the structure of the present invention. The greatest force is at the apex of the force triangle. With the tower design of the present invention, only a distractive force is applied to the tissue around the joint, and the apex of the distraction force is distant from the joint, so there is less force at the joint, and therefore less damage to the joint tissues. Thus, less compressive force is required to be placed on the joint to obtain the same results. The orthosis stretches the tissue around the joint without compressing the joint itself, which is the conjunction of two or more bones.

BRIEF DESCRIPTION OF THE DRAWINGS

Further features of the present invention will become apparent to those skilled in the art to which the present invention relates from reading the following specification with reference to the accompanying drawings, in which:

FIG. 4 is an enlarged view partially in section of the winch mechanism of the orthosis of FIG. 1;

FIG. 5 is a perspective view of an adjustable orthosis in accordance with a second embodiment of the invention and shown in a flexed position;

FIG. 8 is an enlarged view of an adjustable length support member for an adjustable orthosis in accordance with a third embodiment of the invention;

FIG. 9 is an enlarged view of a portion of an orthosis with another adjustable length support member;

FIG. 13 is a sectional view, taken generally along the line 13—13, illustrating the construction of an arm section of the orthosis of FIG. 11;

FIG. 14 is a sectional view, taken generally along the line 14—14 of FIG. 11, illustrating the construction of a connector section of the orthosis of FIG. 11;

FIG. 17 is a schematic illustration of a drive assembly used in the orthosis of FIG. 16;

FIG. 18 is a fragmentary sectional view of a portion of a one-piece member used in the orthosis of FIG. 16 and illustrating the construction of a connector section of the orthosis.

DESCRIPTION OF PREFERRED EMBODIMENTS

The term "orthosis" is typically used to refer to a brace or other device applied to a portion of the body to correct malalignment of joints. The present invention is an adjustable orthosis for stretching tissue in the human body. In particular, the present invention relates to an adjustable orthosis which can be used for stretching tissue in a body. In the description below, the invention is described as embodied in an orthosis for stretching tissue around a joint, although the invention is not limited thereto.

Figure 1:
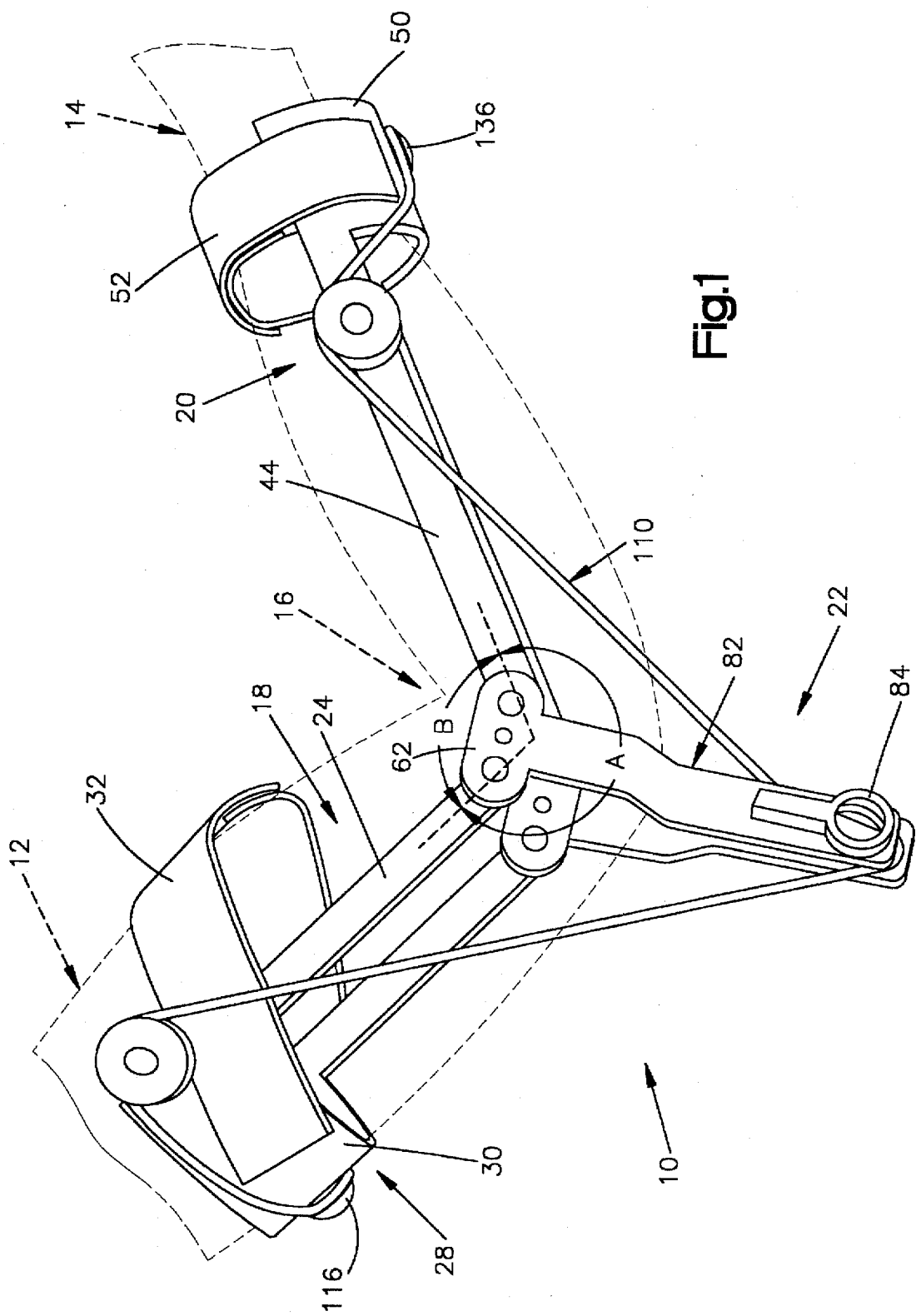
FIG. 1 is a perspective view of an adjustable orthosis of one embodiment of the invention in a flexed position on an arm of a patient and set up to extend an elbow joint.

FIG. 1 illustrates an orthosis 10 in accordance with one embodiment of the present invention on a human limb including an upper arm 12 and a forearm 14 pivotally connected at an elbow joint 16. The orthosis 10 is illustrated as set up to extend (straighten) the elbow joint 16, although it should be understood that the orthosis 10 can also be set up to flex (bend) the elbow joint 16, as will be described later. It should also be understood that the orthosis 10 can be used to extend or flex other joints in the body, such as a knee joint or a wrist joint or ankle joint, with the construction of the orthosis 10 in such case being varied to fit the particular application. The orthosis can be used, for example, to flex the ankle joint to stretch a tight achilles tendon. It is especially useful in obtaining the last degrees of joint extension. The orthosis can be custom made to fit a particular individual, or can be an off the shelf item. The orthosis can also be used, for example, to eliminate contractures or stress soft tissue. It can be used for patients with cerebral palsy, stroke, spastic paralysis, as well as in post-traumatic or post-surgical cases. It can also be used, for example, in therapy after a knee replacement, in which the last five to ten degrees of motion is difficult to obtain without extensive intervention of a therapist.

The orthosis 10 includes a first arm assembly 18, a second arm assembly 20, and an actuator assembly 22 operable to pivot the first arm assembly 18 relative to the second arm assembly 20 to move the joint 16. (As used herein, the term "move a joint" means either to extend the joint or to flex the joint.)

Figure 2:
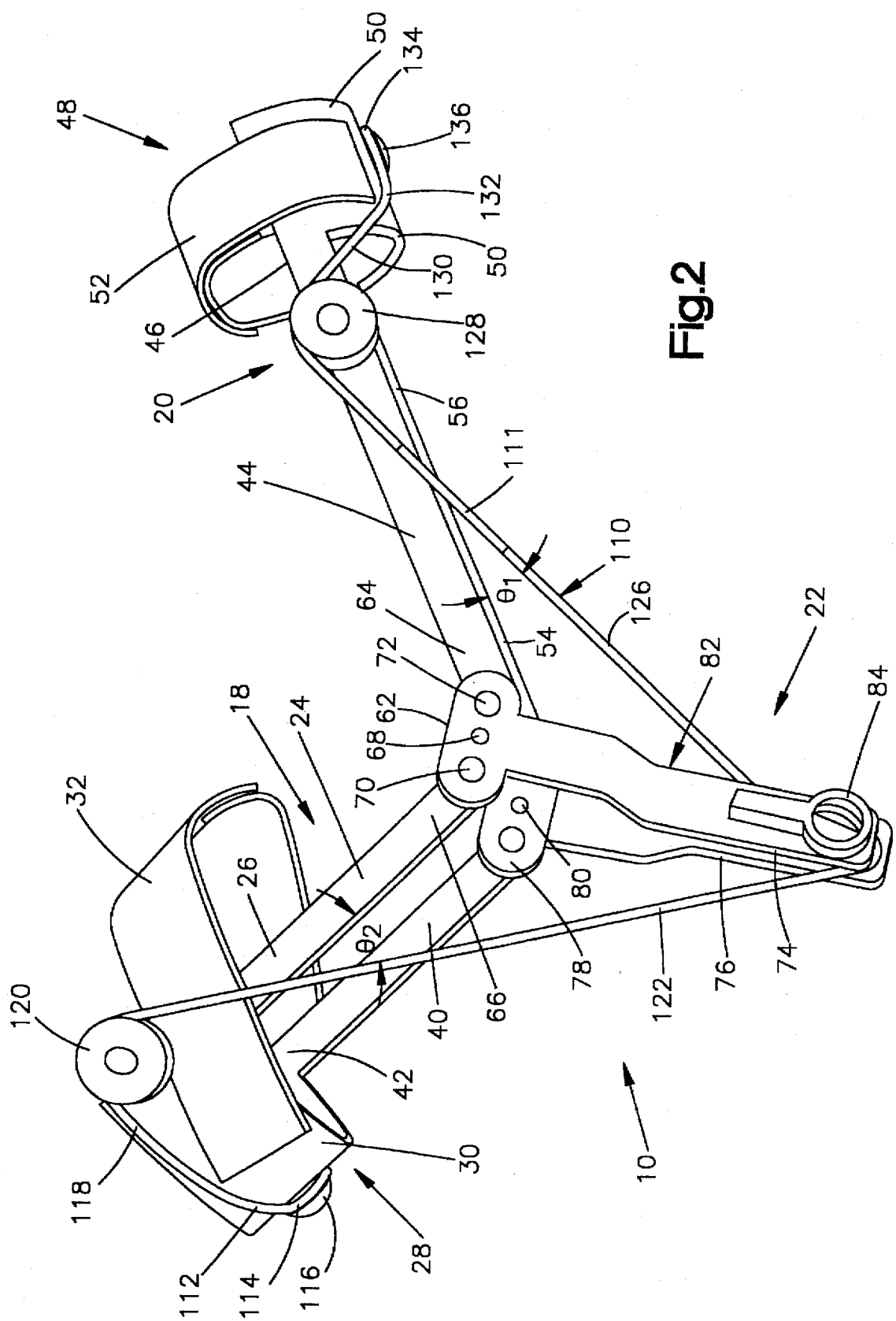
FIG. 2 is a view of the orthosis of FIG. 1 removed from the arm of the patient.

The first arm assembly 18 includes a rigid longitudinally extending cuff arm 24 (FIGS. 1 and 2). To the outer end portion 26 of the arm 24 is attached a first cuff assembly 28. The first cuff assembly 28 includes a rigid cuff portion 30 and a flexible cuff portion 32. The rigid cuff portion 30 extends approximately halfway circumferentially about the upper arm 12, and the flexible cuff portion 32 wraps about the remainder of the upper arm 12. Suitable fastening means such as "Velcro" (trademark) is used to secure the first cuff assembly 28 to the upper arm 12 so that the first arm assembly 18 may apply torque to the upper arm 12.

The first arm assembly 18 also includes a rigid longitudinally extending cuff arm 40, which is shown in FIG. 2 but not in FIG. 1 as it is behind the upper arm 12. An outer end portion 42 of the arm 40 is also attached to the rigid cuff portion 30 of the first cuff assembly 28. The arm 40 extends parallel to the arm 24 and is spaced apart from the arm 24, with the arms 24 and 40 on opposite sides of the upper arm 12 of the limb.

The second arm assembly 20 includes a rigid longitudinally extending cuff arm 44. To an outer end portion 46 of the arm 44 is attached a second cuff assembly 48. The second cuff assembly includes a rigid cuff portion 50 and a flexible cuff portion 52 attached thereto. The rigid cuff portion 50 extends approximately halfway about the forearm 14, and the flexible cuff portion 52 wraps about the remainder of the forearm 14. Suitable fastening means such as "Velcro" (trademark) is used to secure the second cuff assembly 48 about the forearm 14, so that the second arm assembly 20 can apply torque to the forearm 14.

The second arm assembly 20 also includes a rigid longitudinally extending cuff arm 54 which is shown in FIG. 2 but not in FIG. 1. This arm 54 extends parallel to and spaced apart from the arm 44, with the arms 54 and 44 on opposite sides of the forearm 14. An outer end portion 56 of the arm 54 is attached to the rigid cuff portion 50.

The actuator assembly 22 includes a tower 82 which is provided to move the force generating point (that is, the point from which force is directed to the arm assemblies) away from the axis of rotation of the joint to obtain a mechanical advantage. The tower can be any structure which preforms this structure, and need not be the structure shown herein. The tower 82 has a tower connecting portion 62 to which the inner end portions 64 and 66 of the arms 44 and 24 respectively are connected. On the back of the arms 44 and 24 as viewed in FIG. 2 is a pivot plate (not shown) which is fixed by a rivet 68 to the tower connecting portion 62. The tower connecting portion 62 and the pivot plate secure the arm 24 for pivotal movement about a pivot point 70, and the arm 44 for pivotal movement about a pivot 72. Similarly, the tower includes a second tower portion 76 which joins the arms 40 and 54. An inner pivot plate 78 is fixed via a rivet 80 to the second tower portion 76 and provides for pivotal movement of the arms 40 and 54 relative to each other.

Together, the first tower portion 74 and the second tower portion 76, which form the tower 82, support a winch 84 at a substantial distance from the pivot points 70 and 72 of the arms 24 and 44, and at a substantial distance from the pivot points of the arms 40 and 54. (By "substantial" is meant far enough to provide a mechanical advantage as compared to orthoses which apply force at a location adjacent the axis of rotation of the joint. The benefit of this is discussed later herein.) The upper arm 12, elbow joint 16, and forearm 14 define on one side of the joint 16 an inner sector "B" (inside the bend of the limb) which decreases in angle as the joint 16 is flexed. Thus, the inner sector B is disposed on the flexor side of the upper arm 12, elbow joint 16, and forearm 14. The upper arm 12, the elbow joint 16, and the forearm 14 define on the opposite side of the joint 16 an outer sector "A" which decreases in angle as the joint 16 is extended (straightened). Thus, the outer sector A is disposed on the extensor side of the upper arm 12, elbow joint 16, and forearm 14. The tower 82 and the winch 84 are located in the outer sector "A".

The winch 84 includes a drive member 86 (FIG. 4) which extends between the tower portion 76 and the tower portion 74. One end of the drive member 86 is received in a bearing 88 in an opening in the tower portion 76, and the opposite end of the drive member 86 is received in a bearing 90 in a corresponding opening in the tower portion 74. A drum 92 is fixed by a pin 94 to the drive member 86. Wrenching flats 96 are formed on one end of the drive member 86. The opposite end of the drive member 86 is received in a ratchet drive 98 which includes a pawl trigger 100. A leg portion 102 of the ratchet drive 98 is fixed via a suitable fastener such as a screw 104 to the tower portion 76.

A flexible member 110 (FIG. 2) is included in the actuator assembly 22. In the preferred embodiments, the flexible member 110 is a rope. A first end portion 112 of the rope 110 terminates in clip 114 which is fixed via a pin 116 to the rigid cuff portion 30 of the first arm assembly 18. A portion 118 of the rope 110 wraps around a pulley 120. A portion 122 of the rope extends from the pulley 120 to the winch 84. The rope 110 then wraps around the pin 94 (FIG. 4) as at 124 and a portion 126 of the rope 110 extends thence to a pulley 128 on the second arm assembly. A portion 130 of the rope wraps around the pulley 128. The other end portion 132 of the rope 110 terminates in a clip 134 fixed by a pin 136 to the rigid cuff portion 50 of the second cuff assembly 48. Thus, both ends of the rope 110 are fixed to the cuff assemblies, while the middle portion of the rope 110 is windable by the winch 84.

The orthosis 10 is operated to extend a joint such as the joint 16 in the following manner. The first cuff assembly 28 is fastened about the upper arm 12 tightly enough that the first arm assembly 18 may apply torque to the upper arm 12 without having the cuff assembly 28 slide along the upper arm 12. Similarly, the second cuff assembly 48 is fastened securely around the forearm 14 so that the second arm assembly 20 may apply torque to the forearm 14 without the cuff assembly 48 sliding along the forearm 14. The drive member 86 of the winch 84 is then rotated about its axis 106 to wind the rope 110. The rope portions 122 and 126 are partially wound onto the drum 92. Because the rope end 112 is fixed to the first cuff assembly 28, and the other rope end 132 is fixed to the second cuff assembly 48, the cuff assemblies 28 and 48 are drawn toward the winch 84. The first arm assembly 18 pivots about the pivot point 70, and the second arm assembly 20 pivots about the pivot point 72. As the arm assemblies 18 and 20 pivot, the upper arm 12 and forearm 14, to which they are attached, also pivot. This moves or extends the joint 16 as was desired.

Figure 3:
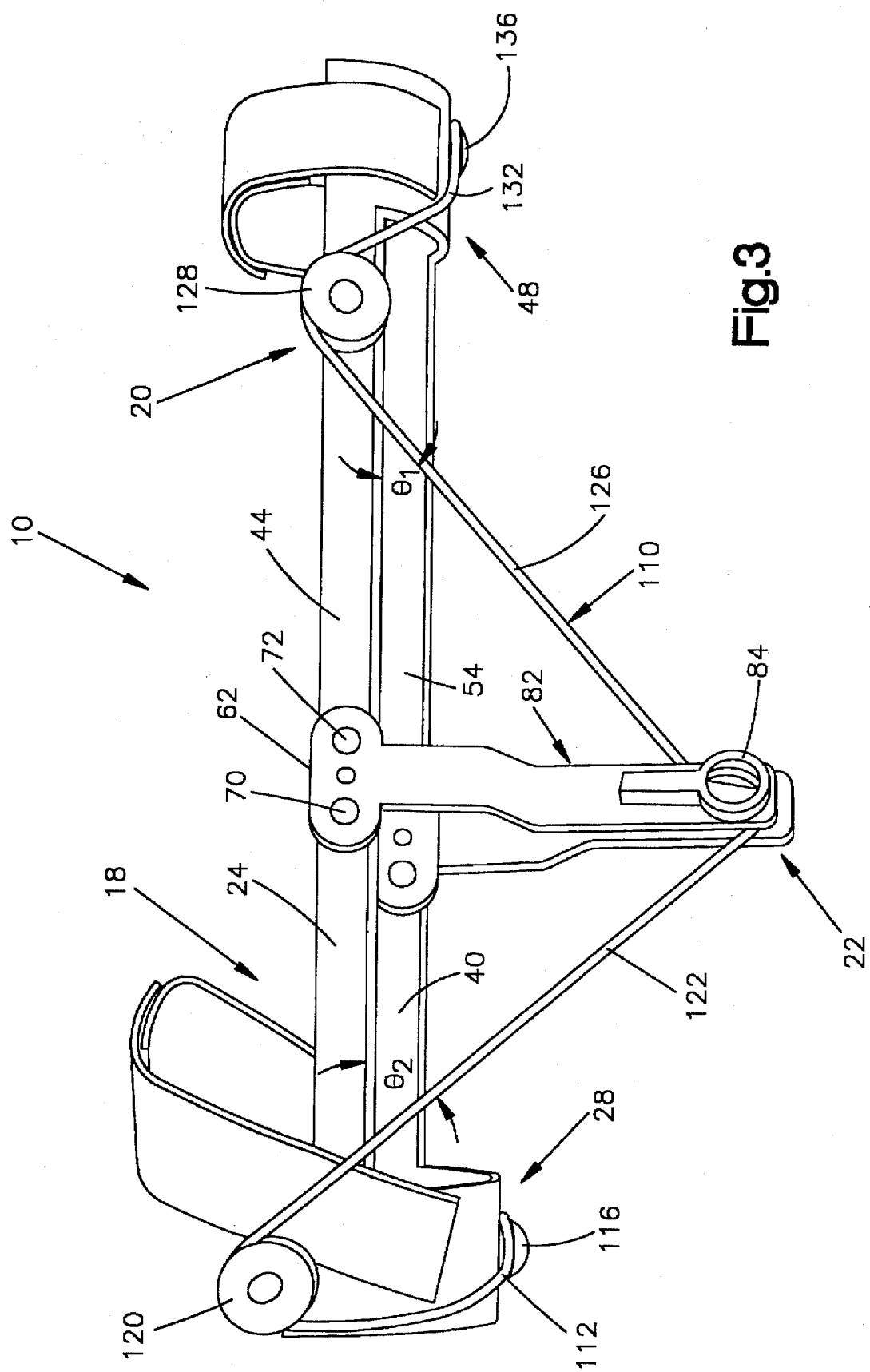
FIG. 3 is a view of the orthosis of FIG. 1 in an extended position.

As the orthosis 10 is adjusted to extend the joint 16 from the relatively flexed position shown in FIG. 2 to the relatively extended position shown in FIG. 3, the acute angle $\Theta_1$ (FIG. 2) between the rope portion 126 and the first arm assembly 20 increases. At the same time, the acute angle $\Theta_2$ (FIG. 2) between the rope portion 122 and the first arm assembly 18 also increases as the orthosis is adjusted from the relatively flexed position shown in FIG. 2 to the relatively extended position shown in FIG. 3.

The torque applied by a cuff assembly to its respective limb portion is equal to (1) the force applied along the rope portion extending from the winch 84 to that arm assembly, times (2) the length of the lever arm of that arm assembly, times (3) the sine of the angle between the rope portion and the arm assembly. For example, referring to FIG. 2, the torque applied to the first arm assembly 18 at the pulley 120 is equal to the force applied along the rope portion 122, times the lever arm (which is equal to the distance between the pivot 70 and the pulley 120), times the sine of the angle $\Theta_1$ between the rope portion 122 and the arm 24 or the arm 40.

As the orthosis 10 is adjusted from a relatively flexed position as viewed in FIG. 2 to a relatively extended position as viewed in FIG. 3, the angle between a rope portion (122 or 126) and its respective arm assembly (18 or 20) increases. Thus, the sine of the angle between the rope portion and the arm assembly also increases. For any given orthosis, the length of the lever arm is a constant. Thus, assuming a constant force applied by the winch 84 pulling on the rope portion 122, a greater amount of torque is applied by the arm assembly to the limb portion as the orthosis 10 is adjusted from a relatively flexed position as viewed in FIG. 2 to a relatively extended position as viewed in FIG. 3.

Since terminal stretching, that is, extension through the last degrees of a range of motion, is the most difficult in a human joint, the orthosis of the present invention is highly advantageous in that the amount of torque available to pivot the upper arm relative to the forearm increases as the joint is extended. The orthosis provides a large straightening force through the full range of motion because it maintains a significant vertical (extension) force vector through the full range of motion. Of course, this assumes a sufficient force applied to and by the winch 84, and it is understood that more force may be needed to turn the winch 84 as the joint is fully extended to overcome the stiffness of the joint.

The force vector representative of the pulling force extending along the flexible member 110 can be resolved into a component extending in a direction parallel to the arm assembly and a component extending in a direction perpendicular to the arm assembly. The force component extending in the direction perpendicular to the arm assembly is representative of the magnitude of the net extension force applied to the arm assembly to extend the joint. This component is equal to the sine of the angle between the flexible member and the arm assembly, times the force in the direction along the flexible member.

The net extension force is therefore directly proportional to the sine of the angle between the flexible member and the arm assembly. Thus, to increase the extension force applied to the arm assembly, the angle can be increased. It can be seen that one way to increase the angle is to increase the distance between the pivot point for the arm assembly and the drive means. Thus, it is evident that the longer the support member or tower, the greater the extension force.

Thus, the structure of the orthosis 10 is clearly advantageous as compared to, for example, a prior art device which applies its force at a location closely adjacent to the joint. For such a device, the distance between the force application point and the pivot point of the arm is very short. Thus, the angle between (a) the arm and (b) a line extending between the cuff assembly and the force generation point, is always extremely small. Accordingly, the amount of torque which can be generated is extremely limited. Thus, having the winch or drive means 84 spaced at a substantial distance from the pivot points 70 and 72 by the tower 82, as in the illustrated embodiments, provides a substantial mechanical advantage.

It can also be seen that, when the winch 84 pulls on the flexible member 110, a reaction force is developed in the rigid tower or support member 82. The reaction force extends along the tower 82 in the direction from the winch 84 to the pivots 70 and 72 and the to pivots for the arms 40 and 54. The reaction force 84 tends to push in one direction on the inner end portions of the arms 24, 40, 44, and 54, while the pulling force generated by the winch 84 moves the outer end portions of the same arms in the opposite directions. Thus, the actuator assembly 22 simultaneously applies oppositely directed forces to opposite ends of the arm assemblies 18 and 20 to provide an even more efficient pivoting motion to extend the joint 16.

It should be noted that the pulley 120 is in a different position on the first arm assembly 18 than the pulley 128 is on the second arm assembly 20. The location of the pulleys is a matter of design choice. As a pulley is moved farther out along its arm assembly from the pivot point, the lever arm and thus the torque applied to the arm assembly by the winch 84 pulling on the flexible member 110 increases. The pulley is also preferably located as far from the rope end portions as possible in a direction transverse to the longitudinal extent of the arms. For example, the pulley 120 is farther from the pin 116 in a direction transverse to the arm 24, than the pulley 128 is from the pinion 136 in a direction transverse to the arm 44. Moving the pulley farther away in this manner increases the angle between the rope portions and the arm assemblies, thus increasing the available torque.

It should also be noted that the orthoses of the present invention are suitable to hyperextend a joint, also.

Preferably, the orthosis is constructed so that the joint when fully extended is hyperextended by 5° to 7°. This provides the fullest range of motion desired. This can be accomplished by construction of the pivotal connection between the arm assemblies to allow for such hyperextension.

Figure 6:
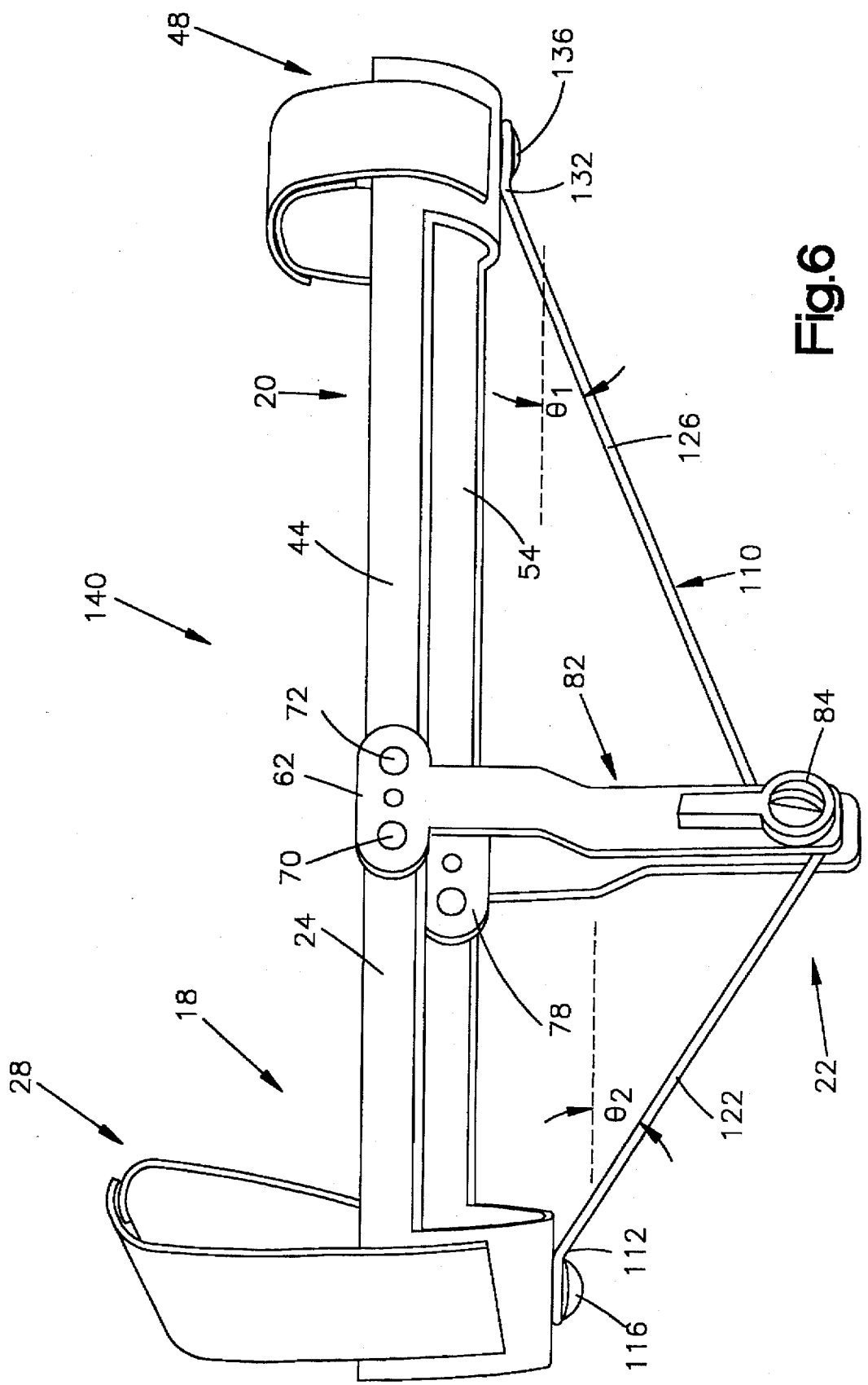
FIG. 6 is a view of the orthosis of FIG. 5 in an extended position.

A second embodiment of the invention is illustrated in FIGS. 5 and 6, in which parts which are the same as in the first embodiment are given the same reference numerals. An orthosis 140 includes a flexible member 110 which does not extend around pulleys but extends directly from the winch 84 to the cuff assemblies 28 and 48. The orthosis 140 is, like the orthosis 110, adjustable between a relatively flexed position as viewed in FIG. 5 and a relatively extended position as viewed in FIG. 6. Manual actuation of the winch 84 draws or pulls the rope portions 122 and 126 to wind them on the winch 84, shortening the distance between the cuff assemblies 28 and 48 and the winch 84. Because the inner ends of the arms 24, 40, 44, and 54 are pivotally mounted to the tower 82, the arm assemblies 18 and 20 pivot relative to each other to move the joint 16 into a more extended position.

With the orthosis 140, again, the acute angle $\Theta_1$ between the rope portion 126 and the second arm assembly 120, and the acute angle $\Theta_2$ between the rope portion 122 and the first arm assembly 18, increase in degree as the orthosis 140 is adjusted from the more flexed position shown in FIG. 5 to the more extended position shown in FIG. 6. Furthermore, placement of the winch or drive means 84 at substantial distance from the pivot points 70 and 72, as in the embodiment illustrated in FIGS. 5 and 6, ensures that a significant mechanical advantage is obtained.

Figure 7:
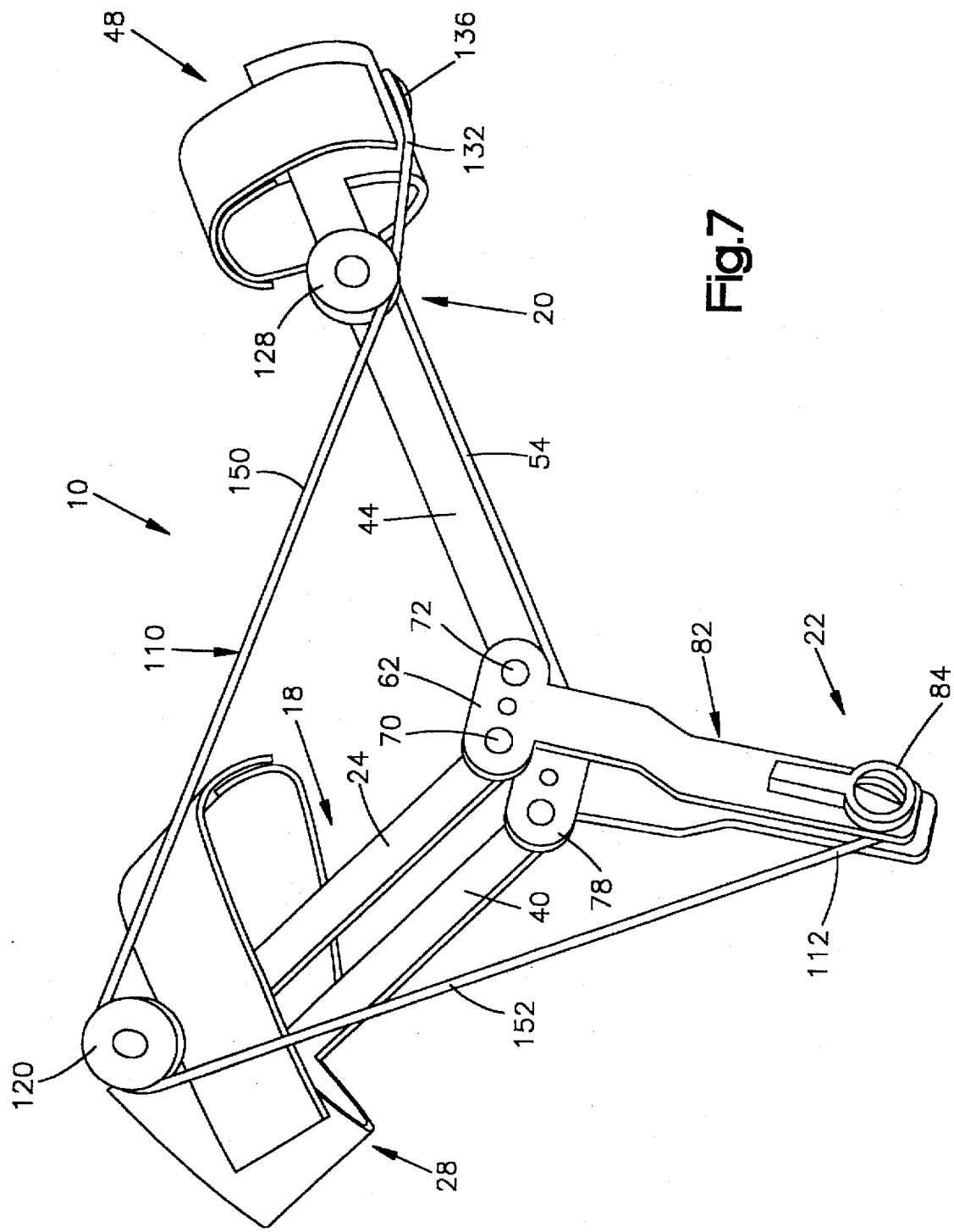
FIG. 7 is a view of the orthosis of FIG. 1 set up to flex a joint.

The orthosis 10 is illustrated in FIGS. 1 through 4 as being used to extend a joint. The orthosis 10 can also be used to flex a joint as illustrated in FIG. 7. This is done by rerouting the flexible member 110. The end portion 132 (FIG. 7) of the flexible member 110 remains fixed by the pin 136 to the second cuff assembly 48. A portion 150 of the rope 110 then extends underneath the pulley 128 over to the pulley 120. The rope 110 then extends around the pulley 120 and a portion 152 of the rope 110 extends to the winch 84. The end portion 112 of the rope 110 is tied or otherwise fixed to the winch 84.

When the winch 84 is then manually operated, the rope 110 will be wound to the drum of the winch 84. The second cuff assembly 48 will be drawn toward the first cuff assembly 28. Because the inner ends of the arm assemblies 18 and 20 are fixed to the tower 82 the arm assemblies 18 and 20 pivot relative to each other, decreasing the included angle between them. Since the arm assemblies 18 and 20 are fixed to the limb portions 12 and 14, the joint 16 is flexed.

As noted above, the net extension force is therefore directly proportional to the sine of the angle between the flexible member and the arm assembly. One way to increase the angle is to increase the distance between the pivot point for the arm assembly and the drive means. Accordingly, in a third embodiment of the invention, the actuator assembly for pivoting the first and second arm assemblies 18 and 20 includes, in place of the tower 82 and the winch 84, a variable length tower with a pulley at its outer end. Extending the variable length tower to move the pulley farther away from the pivot points of the arm assemblies 18 and 20, causes the arm assemblies 18 and 20 to pivot relative to each other to flex the joint 16.

The variable length feature of the tower assembly can be obtained in many different ways. FIGS. 8 and 9 illustrate two ways of constructing the variable length tower assembly.

In FIG. 8, a tower assembly 160 includes a fixed portion 162 (only a part of which is shown) upon which the arm assemblies 18 and 20 (not shown) are pivoted. A tower portion 164 is movable axially relative to the fixed tower portion 162. A pneumatic ram assembly 166 is actuatable in an axial direction as indicated by arrow 168 upon the introduction of fluid under pressure through a fluid supply line 170. A pulley is mounted for rotation on the outward end of the movable tower portion 164. The flexible member or rope 110 (not shown) passes over the pulley and is not fixed to the pulley. Upon the introduction of fluid under pressure through the fluid supply line 170, the pneumatic ram assembly 166 causes the movable tower portion 164 to move outwardly relative to the fixed tower portion 162. Such motion causes the pulley to move away from the pivot points for the arm assemblies 18 and 20. This exerts a pulling force on the flexible member 110 which extends around the pulley. This pulling force, as above, causes the arm assemblies 18 and 20 to pivot relative to each other to extend the joint 16 to which the orthosis is attached.

Fluid under pressure may be supplied to the supply line 170 in any known manner. One specific apparatus, which is operable by hand and thus usable by the patient, is illustrated in FIG. 8 and includes a piston 174 disposed within a chamber 176. An arm 178 connects the piston 174 to a handle 180 which is pivotally mounted at 182 to a base 184. When the handle 180 is moved (squeezed) toward the base 184 in the direction indicated by arrow 186, the piston 174 forces air through the fluid supply line to supply the pneumatic ram assembly 166. It should be understood that any means of supply fluid under pressure could suitably also be used.

Another manner of construction for an extendible tower assembly is indicated schematically in FIG. 9. The tower assembly 190 includes a fixed tower portion 192 having a threaded member 194 projecting outwardly therefrom, and a movable tower portion 196 having a threaded member 198 projecting inwardly therefrom. A sleeve nut 200 threadedly engages the threaded members 194 and 198 and has a handle portion or thumbwheel 202 extending radially therefrom. A pulley (not shown) is mounted on the movable tower portion 196 as in the construction illustrated in FIG. 8. Similarly, the fixed tower portion 192 is connected to the first and second arm assemblies. When the handle portion 202 is manually rotated about the longitudinal axis of the extendible tower 190, the movable tower portion 196 moves axially relative to the fixed tower portion 192. Accordingly, axial movement of the movable tower portion 196 away from the fixed tower portion 192 produces a pulling force on the rope 110, causing the first and second arm assemblies 18 and 20 to pivot relative to each other, thus extending the joint 16.

Figure 10:
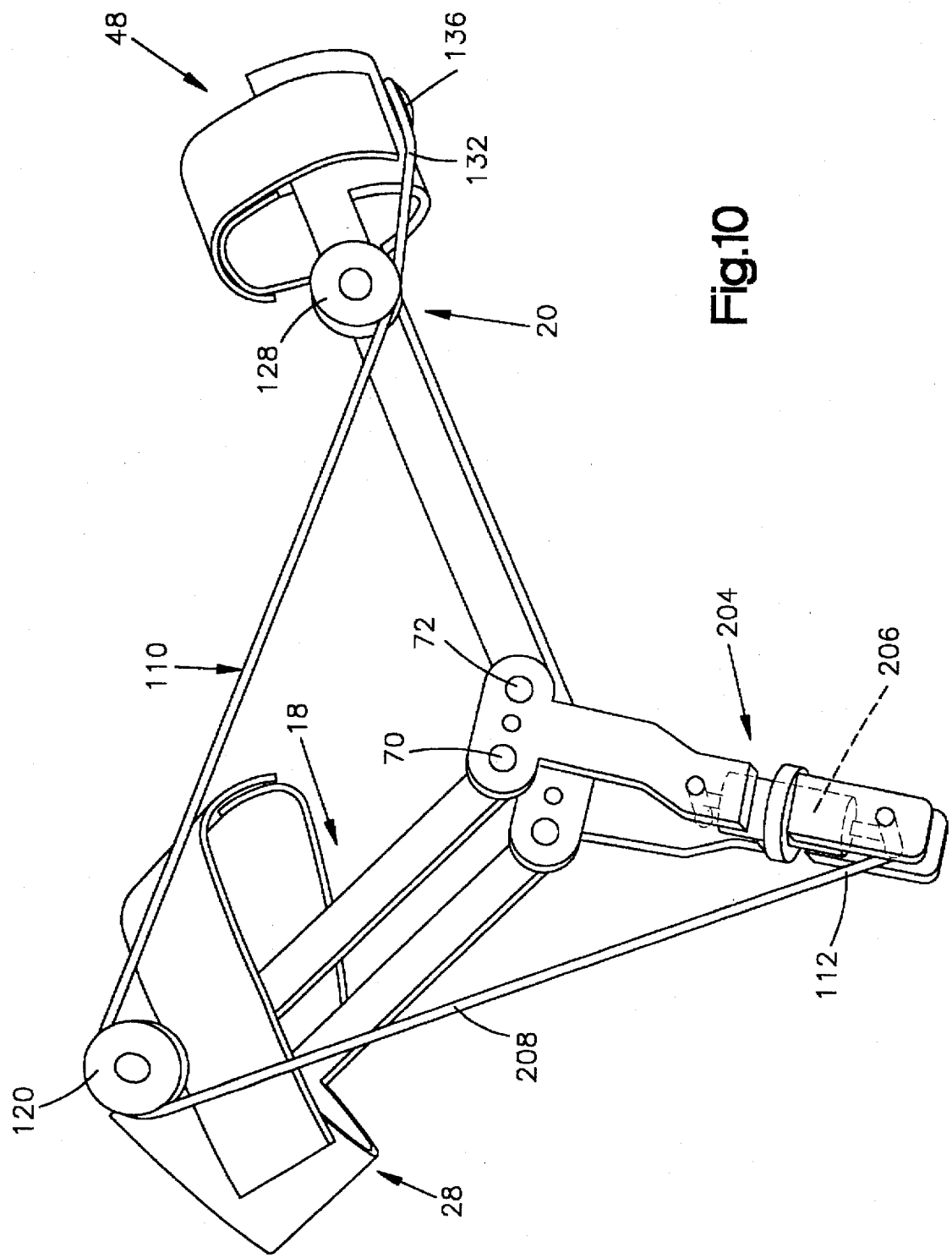
FIG. 10 is a view of the orthosis of FIG. 9 set up to flex a joint.

An extendible tower assembly can also be used in an orthosis set up to flex a joint rather than an extended joint. FIG. 10 illustrates such a construction. The one end portion 132 of the rope 110 is fixed to one cuff assembly 40. However, the opposite end portion 112 of the rope 110 is fixed to an outer end 206 of the extendible tower 204. When the extendible tower assembly 204 of the orthosis shown in FIG. 10 is made longer, increasing the distance between the pulley 206 and the pivotal connection with the arm assemblies 18 and 20, a pulling force is generated on the rope portion 208, drawing the cuff assemblies 28 and 40 closer to each other. This causes the arm assemblies 18 and 20 to pivot relative to each other to decrease the angle between them, thus flexing a joint to which the orthosis is attached. Thus, it can be seen that the extendible tower assembly is usable in both flexion and extension modes, just as the tower with a winch or other type of drive means is usable in both flexion and extension modes.

It should be noted that other configurations of the illustrated orthoses are possible when the orthoses are set up for flexion. The flexible member 110 can be routed in other ways to achieve flexion. Similarly, extension can be achieved by the illustrated of those when the flexible member 110 is routed differently, by moving pulleys or attachment points. Such variations on the illustrated embodiments, within the ordinary skill of the art, are part of the present invention and are covered by the appended claims.

In a further improvement, the illustrated orthoses may also include means for monitoring the amount of force transmitted through the flexible member 110 to the arm assemblies 18 and 20. Further, the orthoses may include relief means for limiting the amount of force transmitted to the arms 18 and 10. Such means are indicated schematically at 210 in FIG. 4 as being in the line of force transmission between the drive member 86 and an extension 216 thereof. The force monitoring or limiting means can be something as simple as a torque wrench applied to the drive member 86, or it can be a more complex mechanical structure, or it can be electronically controlled or operated. Thus, the box 210 illustrates schematically the provision or placement of force measuring and/or limiting means within the force path between the point at which the actuator is manually actuated and the cuff assemblies which transmit force to the arm portion. Such means can also be included, for example, within the flexible member itself, or at the pivot points, or at any other suitable location. Provision of such force monitoring or limiting means is within the skill of the art and thus is not described further herein.

The arms 24, 40, 44, and 54 are rigid members made of, for example, aluminum or stainless steel. The arms are rigid so as to be able to transmit the necessary forces. Similarly, the tower 82 and any extensible tower is also made of suitable material such as aluminum or stainless steel in order to provide a rigid structure capable of transmitting the necessary forces. It should be understood that any material of sufficient rigidity can be used, including a polymeric or composite material.

It should be understood that the winch 84 is not the only possible mechanism which can be used for tightening the flexible member 110. Rather, any other suitable mechanism can be used for that purpose, such as a screw mechanism, a pneumatic or fluid operated mechanism, a motor drive, etc. Furthermore, any structure other than the tower 82 can be employed, which will move the point of force application away from the axis of rotation of the joint. Again, the hinge structure shown can, of course, be replaced by, for example, a flexible piece of plastic or some other hinge mechanism. Accordingly, the present invention is not limited to the use of a winch or a tower or hinge strictly as shown.

It should also be noted that the flexible member 110 can include or can be replaced by a resilient member, such as an elastic portion or a spring loading structure. This provides the patient with some ability to bend or flex the joint while the orthosis is attempting to extend the joint. In effect, the patient's muscles work against the force of the orthosis and providing further exercise for the muscles. The flexible member, when tensioned by the drive means, is stretched even more by the patient pulling on it in the opposite direction—resisting the extension force applied by the winch. He pulls through the range of motion. After the range of motion is obtained, the device can also be used for exercise, to lessen pain, and to retain the range of motion at any given point. The modifications to the structure shown in the drawings are obvious to one of ordinary skill, and so are shown only schematically in the drawings, as indicated by the flexible member portion 111 in FIG. 1 which is a length of the rope 110 which is to some extent stretchable or elastic as opposed to the remainder thereof which firmly transmits the extension force to the arm assemblies.

Any of the orthoses of the present invention may also include means for providing three distinct areas of application of force to the limb. In addition to the two cuff assemblies which apply force at locations as far distant as possible from the joint to increase mechanical advantage, means can be provided for applying force in the opposite direction to the area of the limb adjacent the joint. This would include, for example, a cup on the outside of the elbow or knee or straps extending around the elbow or knee. Such modification can easily be made in accordance with the teachings of the prior art, for example as shown in the Best, Brown, or Lonardo patents identified above.

Figure 11:
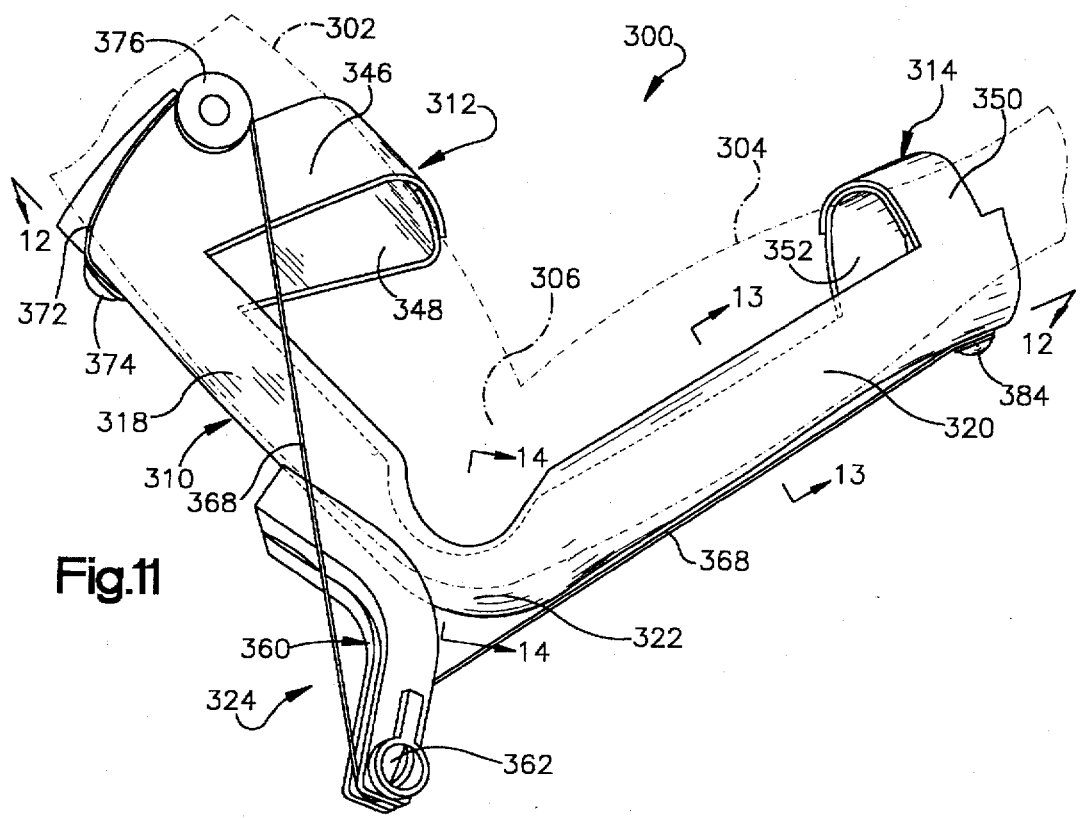
FIG. 11 is a perspective view of an adjustable orthosis of one embodiment of the invention in a flexed position on an arm of a patient and set up to extend an elbow joint.

An orthosis or apparatus 300 forming another embodiment of the invention is illustrated in FIG. 11. The orthosis 300 is operable to effect relative movement between first and second body portions interconnected by a joint. Thus, the orthosis 300 is operable to effect relative movement between an upper arm 302 and a forearm 304. The upper arm 302 and forearm 304 are interconnected by an elbow joint 306.

Although the orthosis 300 is illustrated in FIG. 11 in association with an elbow joint 306 and arm of a person, it should be understood that an orthosis having the same general construction as the orthosis 300 could be used in association with a knee joint and leg of a person. It is also contemplated that an orthosis constructed in accordance with the embodiment of the invention illustrated in FIG. 11 could be used with a wrist joint, or an ankle joint, or a knuckle of a human patient.

In accordance with one of the features of the embodiment of the invention illustrated in FIG. 11, the orthosis 300 includes a one-piece member 310 (FIG. 11). The one-piece member 310 is formed as an elongated strip which has a generally U-shaped cross-sectional configuration and extends along the extensor side of the arm of a human patient. The one-piece member 310 is connected with the extensor side of the upper arm 302 of a person by a cuff 312. The one-piece member 310 is connected with the extensor side of the forearm of a person by a cuff 314.

The one-piece member 310 includes a linear cuff arm section 318 which engages the upper arm 302. The one-piece member also includes a second linear cuff arm section 320 which engages the forearm 304 of a person. A connector section 322 is integrally formed as one-piece with the cuff arm sections 318 and 320 and extends between the cuff arm sections.

An actuator assembly 324 is connected with the cuff arm sections 318 and 320. The actuator assembly 324 is operable to move the cuff arm sections 318 and 320 relative to each other. As the cuff arm sections 318 and 320 are moved relative to each other by the actuator assembly 324, the connector section 322 is flexed or bent and the elbow joint 306 is bent. The actuator assembly 324 has the same general construction and mode of operation as the actuator assembly 22 of the embodiment of the invention illustrated in FIG. 1.

In accordance with one of the features of the invention, the upper and lower cuff arm sections 318 and 320 (FIG. 12) and the connector section 322 are formed of a single piece of polymeric material. The single piece of polymeric material is molded or vacuum formed to integrally form the upper and lower cuff arm sections 318 and 320 and the connector section 322 as one-piece.

The lower cuff arm section 320 has arcuate inner and outer side surfaces 330 and 332 (FIG. 13) having a common center of curvature, indicated at 334 in FIG. 13. The arcuate inner side surface 330 of the lower cuff arm section 320 is held in engagement with the forearm 304 by the cuff 314 (FIG. 11). The center of curvature 334 (FIG. 13) of the inner and outer side surfaces 330 and 332 of the lower cuff arm section 320 is disposed within the spatial envelope occupied by the forearm 304. The arcuate inner side surface 330 of the lower cuff arm section 320 forms a linear portion of a trough in which the forearm 304 is received. The lower cuff arm section 320 is disposed in the outer sector and is disposed in engagement with the extensor side of the forearm 304.

The upper cuff arm section 318 (FIGS. 11 and 12) has the same arcuate configuration as the lower cuff arm section 320. Thus, the upper cuff arm section 318 has an arcuate inner side surface 336 (FIG. 12) which forms a linear portion of a trough in which the upper arm 302 is disposed. The center of curvature of the inner side surface 336 of the upper cuff arm section 318 is disposed in the spatial envelope occupied by the upper arm 302 (FIG. 11). Although the upper cuff arm section 318 could have a different radius of curvature than the lower cuff arm section 320, in the illustrated embodiment of the invention, the upper cuff arm section 318 is formed with the same radius of curvature as the lower cuff arm section. The upper cuff arm section 318 is disposed in the outer sector and is disposed in engagement with the extensor side of the upper arm 302.

The connector section 322 extends between and is integrally formed as one-piece with the upper cuff arm section 318 and the lower cuff arm section 320. The connector section 322 has the same thickness as the cuff arm sections 318 and 320. However, the width of the connector section is less than the width of the cuff arm sections 318 and 320 (FIGS. 11–14).

The connector section 322 is disposed in the outer sector and is disposed along the extensor side of the elbow joint 306. The connector section 322 has an arcuate inner side surface 338 and an arcuate outer surface 340 (FIG. 14). A center of curvature 342 of the arcuate inner side surface 338 of the connector section 322 is disposed within a spatial envelope occupied by the elbow joint 306. The connector section 322 is deflected upon bending of the elbow joint 306.

The arcuate inner side surface 338 of the connector section 322 is formed as one piece with and as a continuation of the inner side surfaces 330 and 336 of the cuff arm sections 320 and 318. The inner side surface 336 of the upper cuff arm section 318, the inner side surface 338 of the connector section 322 and the inner side surface 330 of the lower cuff arm section 320 cooperate to form a continuous trough in which a patient's arm is received. The trough has a generally U-shaped cross sectional configuration (FIGS. 13 and 14) along its length.

When the elbow joint 306 is in an extended condition, the connector section 322 has a linear configuration and is coaxial with the linear upper and lower cuff arm sections 318 and 320. As the elbow joint 306 is flexed, as shown in FIG. 11, a smooth continuous arcuate bend is formed along the entire length of the connector section 322. The arcuate bend formed in the connector section 322 is a smooth continuation of the linear cuff arm sections 318 and 320.

If desired, the material forming the connector section 322 could be thinner than the material forming the cuff arm sections 318 and 320. As the elbow joint 306 is flexed, the distance between the elbow joint and the inner side surface 338 of the connector section 322 will vary. The connector section 322, upper cuff arm section 318 and lower cuff arm section 320 are all disposed in the outer sector along the extensor side of the upper arm 302, forearm 304 and elbow joint 306.

The connector section 322 is offset from the axis about which the elbow joint 306 is bent. This enables the cuffs 312 and 314 to tension the soft tissue in the elbow joint 306 as the elbow joint is bent in extension. Thus, as the elbow joint 306 is bent in extension and the connector section is straightened, the distance between the ends of the cuff arm sections 318 and 320 connected to the connector section 322 increases. As the distance between the ends of the cuff arm sections 318 and 320 increases, force is transmitted from the cuff arm sections through the cuffs 312 and 314 to the upper arm 302 and forearm 304. This force tensions the soft tissue in the elbow joint 306.

When the elbow joint 306 is in the flexed condition shown in FIG. 11, the connector section 322 has a longitudinally curving configuration. As the elbow joint is bent in extension, the connector section 322 is bent toward a linear longitudinal configuration. The width of the connector section 322 is less than the width of the cuff arm sections 318 and 320 to facilitate bending of the one-piece member 310 at the connector section. As the connector section 322 is straightened, the soft tissue in the elbow joint 306 is distracted.

As the elbow joint 306 is moved between extended and flexed conditions, the connector section 322 is bent by relative movement between the upper cuff arm section 318 and lower cuff arm section 320. However, the longitudinal central axis of the connector section 322 is, at all times, an extension of the longitudinal central axes of the upper cuff arm section 318 and the lower cuff arm section 320. Thus, when the elbow joint 306 is fully extended and the one-piece member 310 has a linear configuration, the connector section 322 has a linear configuration and the central axis of the connector section is coincident with the longitudinal central axes of the upper and lower cuff arm sections 318 and 320. When the elbow 306 is flexed and the one-piece member 310 is bent to the condition shown in FIG. 11, the connector section 322 has an arcuately curved longitudinal central axis which forms a continuation of the longitudinal central axes of the upper and lower cuff arm sections 318 and 320.

In the embodiment of the invention illustrated in FIG. 11, the cuff 312 includes a pair of straps 346 and 348 which are interconnected by a suitable fastener. Specifically, the cuff straps 346 and 348 are interconnected by "Velcro" (trademark). The cuff 314 also includes a pair of straps 350 and 352. The straps 350 and 352 may be interconnected by any suitable fastener. In the illustrated embodiment of the invention, the straps 350 and 352 are interconnected by "Velcro" (trademark).

Figure 12:
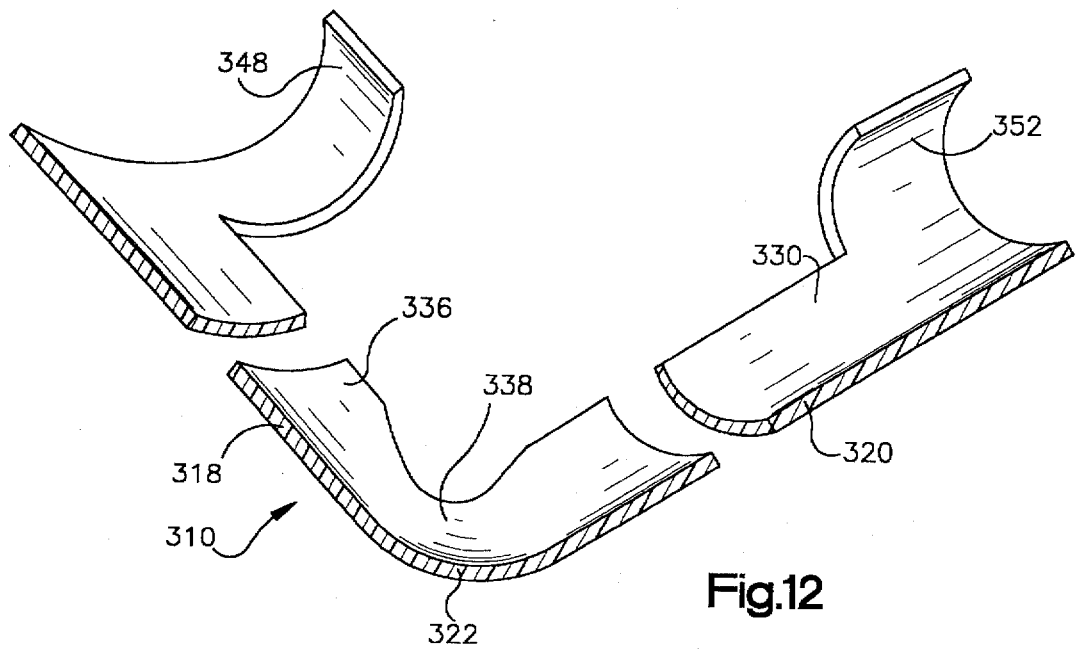
FIG. 12 is a fragmentary sectional view, taken generally along the line 12—12 of FIG. 11, illustrating a one-piece member which forms a portion of the orthosis of FIG. 11.

The cuff straps 346 and 348 for the cuff 312 and the cuff straps 350 and 352 for the cuff 314 are integrally formed as one piece with the one-piece member 310. Thus, the cuff strap 348 of the cuff 312 is formed as one-piece with and extends outward from the upper cuff arm section 318 (FIG. 12). Similarly, the cuff strap 352 is integrally formed with and extends outward from the lower cuff arm section 320. The cuff straps 346 and 350 are integrally formed with the cuff arm sections 318 and 320 in the same manner as are the cuff straps 348 and 352. However, the cuff straps could be formed separately from the cuff arm sections 318 and 320 if desired.

The actuator assembly 324 has the same construction and general mode of operation as the actuator assembly 22 of FIG. 1. Thus, the actuator assembly 324 includes a tower 360 which is disposed in the outer sector and is fixedly secured to the upper cuff arm section 318. A drive assembly 362 is disposed on an outer end portion of the tower 360. The drive assembly 362 has the same general construction and mode of operation as the winch 84 of FIG. 1. However, it should be understood that other known drive mechanisms could be used as the drive assembly 362. For example, one of the drive mechanisms illustrated in FIGS. 8, 9 and 11 could be used to tension the rope 368.

The actuator assembly 324 includes a flexible member a rope 368 which is connected with the drive assembly 362 and outer end portions of the upper and lower cuff arm sections 318 and 320. Thus, an end portion 372 of the flexible member or rope 368 is connected with the upper cuff arm section 318 by a suitable fastener 374 (FIG. 11). The rope 368 extends around a pulley 376 to the drive assembly 362. The pulley 376 is rotatably mounted on the upper end portion of the cuff arm section 318.

An opposite end portion 382 of the flexible member or rope 368 is fixably secured to an outer end portion of the lower cuff arm section 320 by a suitable fastener 384. The rope 368 extends from the fastener 384 to the drive assembly 362. Operation of the drive assembly 362 results in tensioning of the flexible member or rope 368. Tensioning the rope 368 transmits force to the outer end portions of the upper and lower cuff sections 318 and 320 to bend the elbow joint 306 in extension. As this occurs, the connector section 322 is straightened.

Figure 15:
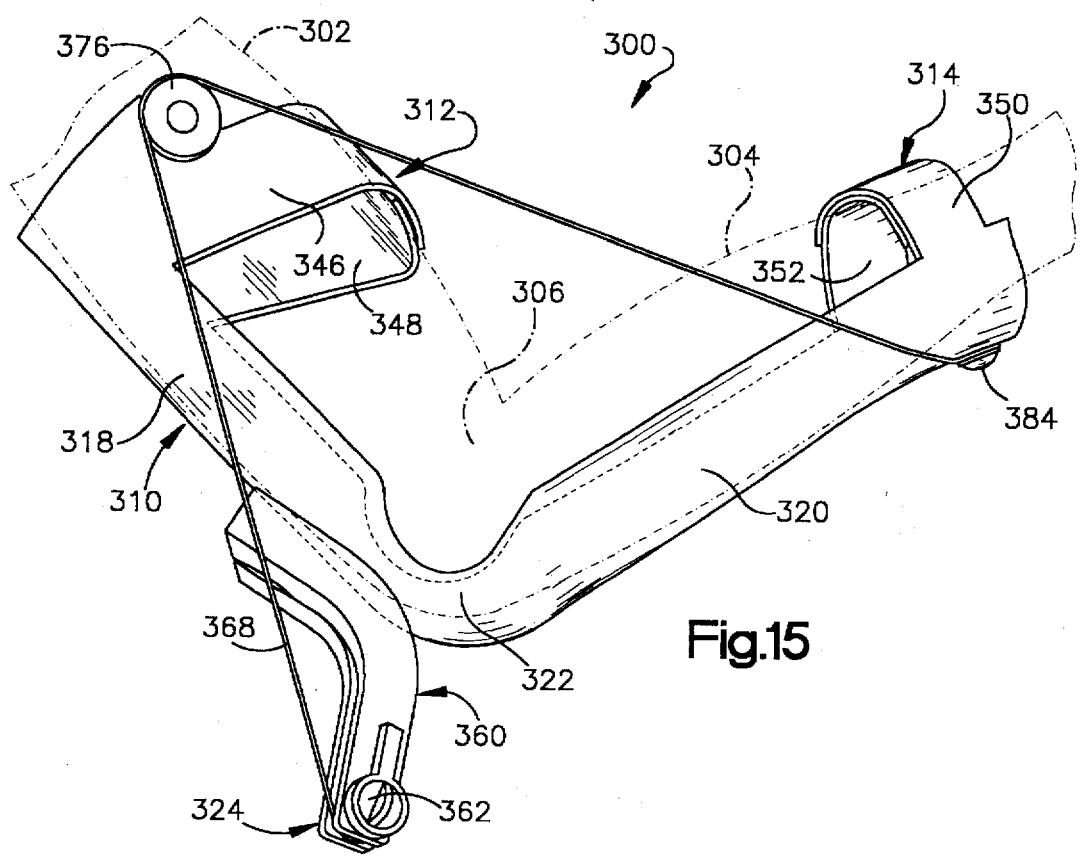
FIG. 15 is a view of the orthosis of FIG. 11 set up to bend an elbow joint in flexion.

The orthosis 300, like the orthosis 10 of FIG. 1, can be used to bend the elbow joint 306 in flexion. When the elbow joint 306 is to be bent in flexion, the path along which the rope 368 extends is changed from the path shown in FIG. 11 to the path shown in FIG. 15. Thus, the rope 368 is shown in FIG. 15 as extending from the drive assembly 362 around the pulley 376 on the upper cuff arm section 318 to the fastener 384 at the outer end of the lower cuff arm section 320. Upon operation of the drive assembly 362, the rope 368 transmits force to the upper and lower cuff arm sections 318 and 320 to bend the elbow joint 306 in flexion.

Figure 16:
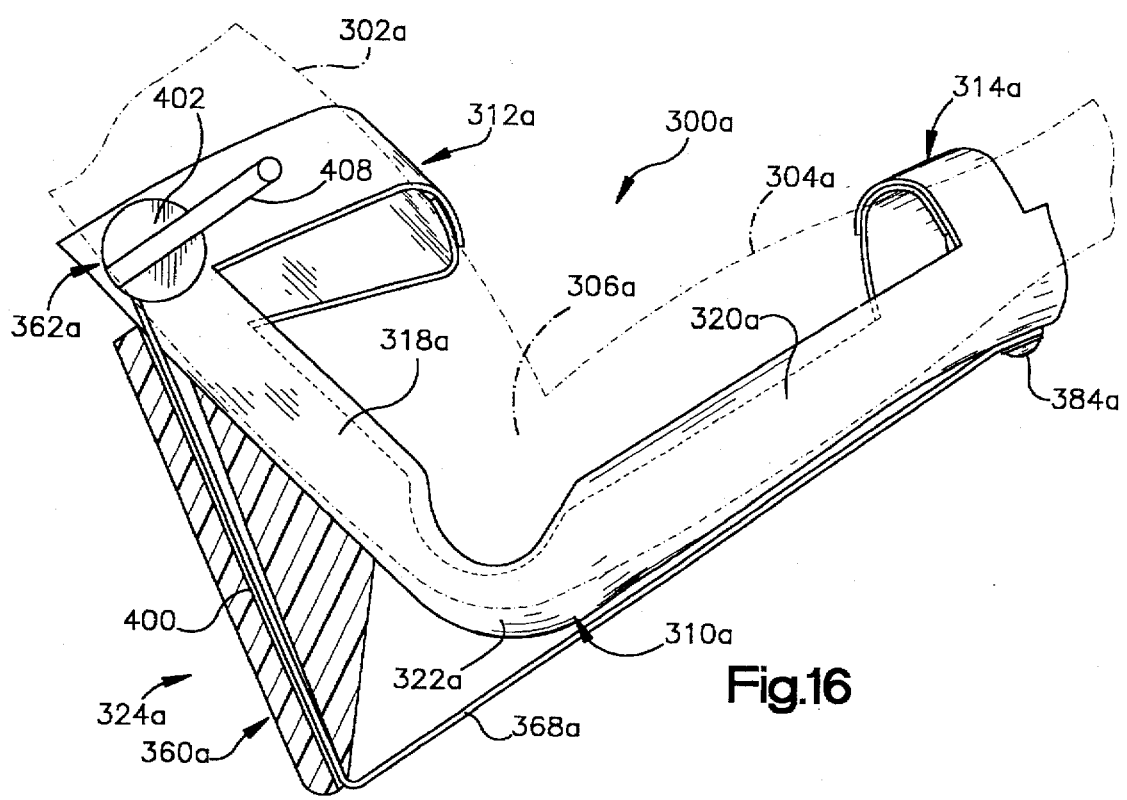
FIG. 16 is a perspective view of an adjustable orthosis in accordance with another embodiment of the invention and set up to bend an elbow joint in extension.

In the embodiment of the invention illustrated in FIG. 11, the actuator assembly 324 has the same general construction as the actuator assembly 22 of FIG. 1. In the embodiment of the invention illustrated in FIGS. 16–18, the actuator assembly has a somewhat different construction. Since the embodiment of the invention illustrated in FIGS. 16–18 is generally similar to the embodiment of the invention illustrated in FIGS. 11–15, similar numerals will be utilized to designate similar components, the suffix letter "a" being associated with the numerals of FIGS. 16–18 to avoid confusion.

An orthosis or apparatus 300a (FIG. 16) is used to effect relative movement between an upper arm 302a and a forearm 304a to bend an elbow joint 306a. The orthosis 300a includes a one-piece member 310a which is connected with the extensor side of the upper arm 302a by a cuff 312a. A second cuff 314a connects the one-piece member 310a with the extensor side of the forearm 304a.

The one-piece member 310a includes an upper cuff arm section 318a and a lower cuff arm section 320a. A connector section 322a is integrally formed as one-piece with the upper and lower cuff arm sections 318a and 320a. Straps of the cuffs 312a and 314a are integrally formed as one piece with the upper cuff arm section 318a and lower cuff arm section 320a.

In accordance with a feature of this embodiment of the invention, an actuator assembly 324a includes a tower 360a. The tower 360a is formed by a single, generally triangular, block of polymeric material. The tower 360a is fixedly connected with the upper cuff arm section 318a and is disposed in the outer sector. A channel 400 extends through the block forming the tower 360a. The channel 400 has a longitudinal central axis which is skewed at an acute angle to a longitudinal central axis of the upper cuff arm section 318a. A flexible member or rope 368a extends through the channel 400.

If desired, a pulley could be mounted on the outer end of the tower 360a to facilitate movement of the rope 368a into the channel 400. Although the illustrated channel 400 has a cylindrical configuration, the channel could be formed as an open groove along the outer side of the block of polymeric material forming the tower 360a.

One end of the rope 368a is connected with a drive assembly 362a. The drive assembly 362a is mounted on the upper cuff arm section 318a adjacent to the cuff 312a. The opposite end of the rope 368a is connected with the outer end portion of the lower cuff arm section 320a by a fastener 384a.

Although the drive assembly 362a could have many different constructions, one specific drive assembly is a winch 402 (FIG. 17). The winch 402 includes a metal base plate 404 which is fixedly secured to the polymeric material of the one-piece member 310a. In the embodiment of the invention illustrated in FIGS. 16 and 17, the base plate 404 of the winch 402 is mounted on the upper cuff arm 318a adjacent to the cuff 312a.

The winch 402 includes a drum 406 (FIG. 17) which is rotatably mounted on the base plate 404. The rope 368a extends around the drum 406. One end of the rope 368a is fixedly connected with the drum 406. A handle 408 is manually rotatable to rotate the drum 406 and wind the rope 368a around the drum.

A ratchet mechanism 410 is connected with the base plate 404 and the drum 406 to block unwinding of the rope 368a from the drum. The ratchet mechanism 410 includes an externally toothed, circular ratchet wheel 412 which is fixedly secured to the drum 406. A spring biased pawl 414 is pivotally mounted on the base plate 404 and is engageable with ratchet teeth on the wheel 412 to block rotation of the drum 406 in a direction in which the rope is unwound from the drum. However, the pawl 414 merely clicks along the ratchet teeth on the wheel 412 when the handle 408 and drum 406 are rotated in a direction which winds the rope 368a on the drum. A pawl release lever 416 is connected to the pawl 414 and is manually actuatable to disengage the pawl 414 from the ratchet wheel 412. When the pawl 414 is disengaged from the ratchet wheel 412, the drum 406 can be rotated to unwind the rope 368a from the drum.

When the elbow joint 306a is to be bent in extension, the drive assembly 362a is operated to tension the rope 368a. The rope 368a applies force through the drive assembly 362a to the upper end portion of the upper cuff arm section 318a. The rope also applies force to the lower end of the lower cuff arm section 320a. The rope presses against the tower 360a and tends to pull the lower cuff arm section 320a in a clockwise direction relative to the upper cuff arm section 318a. As this occurs, the connector section 322a is straightened and the elbow joint 306a is extended.

If the elbow joint 306a is to be flexed, the rope 368a is run directly from the fastener 384a to the drive assembly 362a. Thus, when the elbow joint 306a is to be bent in flexion, the rope does not extend through the channel 400 (FIG. 16) in the tower 360a. At this time, the rope 368a extends directly from the drive assembly 362a to the fastener 384a on the lower end portion of the lower cuff arm 320a. Therefore, operation of the drive assembly 362a applies force to the upper and lower cuff arm sections 318a and 320a to bend the connector section 322a and bend the elbow joint 306a in flexion.

In the embodiment of the invention illustrated in FIG. 16, the connector section 322a is provided with a plurality of grooves 424 (FIG. 18). The grooves 424 extend completely across the connector section 322a and form relatively weak areas in the connector section 322a to facilitate bending of the connector section. Thus, upon application of force to the cuff arm sections 318a and 320a by operation of the drive assembly 362a, the connector section 322a bends at each of the grooves 424. The segments of the connector section 322a between the grooves 424 remain in their original linear configuration as bending occurs at the grooves 424.

Although only three grooves 424 have been shown in FIG. 18, the connector section 322a could be provided with a greater or lesser number of grooves if desired. For example, a large number of closely spaced grooves could be provided in the connector section 322a. It should be noted that the transverse extent of the connector section 322a, like the connector section 322 of FIG. 11, is less than the transverse extent of the upper and lower cuff arm sections 318a and 320a to further facilitate bending of the connector section.

In the embodiment of the invention illustrated in FIGS. 11–15, the upper and lower cuff arms 318 and 320 are formed by the one-piece member 310. The upper and lower cuff arms 318 and 320 are interconnected by the connector section 322 which is integrally formed as one piece with the upper and lower cuff arms. In the embodiment of the invention illustrated in FIG. 19, the cuff arms are formed separately from the connector section.

Figure 19:
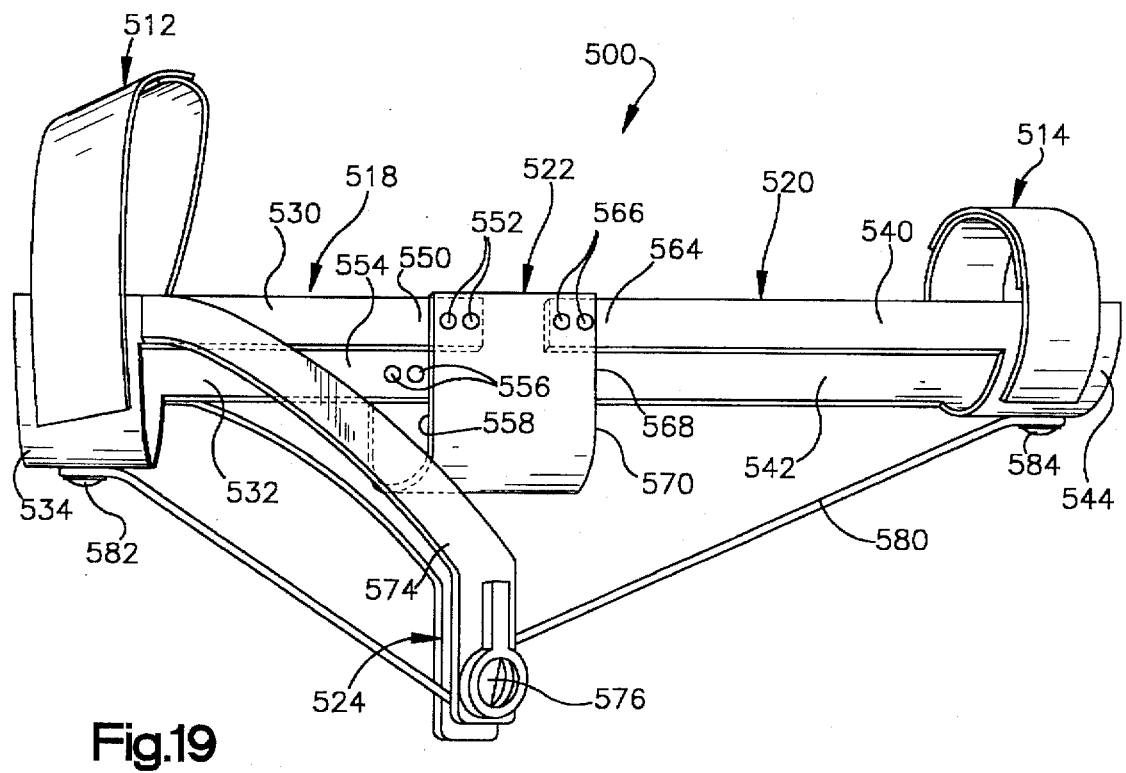
FIG. 19 is a perspective view of an extended orthosis of another embodiment of the invention.

In the embodiment of the invention illustrated in FIG. 19, an orthosis or apparatus 500 includes an upper cuff arm section 518 which is connected with a lower cuff arm section 520 by a connector section 522. A cuff 512 is provided to connect the upper cuff arm section 518 with an upper arm of a person. A cuff 514 is provided to connect the lower cuff arm section 520 with the forearm of a person. An actuator assembly 524 is operable to effect relative movement between the upper and lower cuff arm sections 518 and 520. When this occurs, an elbow joint disposed between an upper arm with which the cuff 512 is connected and a forearm with which the cuff 514 is connected is bent in extension. And the connector section 522 is straightened.

The upper cuff arm section 518 includes a pair of arms 530 and 532 which are interconnected by a generally U-shaped section 534. The U-shaped section 534 is integrally formed as one piece with the arms 530 and 532 of the upper arm section 518. The U-shaped section 534 forms a portion of the cuff 512. The arms 530 and 532 in the U-shaped section 534 may be advantageously formed from a single piece of metal, such as steel or aluminum.

The lower cuff arm section 520 includes a pair of cuff arms 540 and 542 which are interconnected by a U-shaped section 544. The U-shaped section 544 is formed as one piece with the arms 540 and 542. The U-shaped sections 544 forms a portion of the cuff 514. The arms 540 and 542 and U-shaped section 544 are formed from a single piece of metal, such as steel or aluminum.

In accordance with a feature of this embodiment of the invention, the connector section 522 is formed of a flexible polymeric material. The connector section 522 is fixedly connected with an end portion 550 of the arm 530 by fasteners 552. Similarly, an end portion 554 of the arm 532 is connected with the connector section 522 by fasteners 556. The fasteners 552 and 556 are disposed along a generally U-shaped edge portion 558 of the connector section 522.

An end portion 564 of the arm 540 is connected with the connector section 522 by fasteners 566. An end portion 568 of the arm 542 is connected with the connector section 522 by fasteners (not shown) similar to the fasteners 566. The fasteners connecting the arms 540 and 542 with the connector section 522 are disposed along a U-shaped edge portion 570 of the connector section 522.

The actuator assembly 524 has the same general construction and mode of operation as the actuator assembly 22 of FIG. 2. Thus, the actuator assembly 524 includes a tower 574 which is fixedly connected with the arms 530 and 532. A winch 576 is disposed on an outer end portion of the tower 574. A rope 580 is connected with the winch 576. One of the ends of the rope 580 is connected with the U-shaped section 534 by a fastener 582. The opposite end of the rope 580 is connected with the U-shaped section 544 by a fastener 584.

The rope 580 can be connected with the upper cuff arm section 518 and lower cuff arm section 520 in the manner illustrated in FIG. 7 to bend a joint in flexion. Of course, if this was done, pulleys, corresponding to the pulleys 120 and 128 of FIG. 7, would have to be connected with the U-shaped sections 534 and 544.

From the above description of the invention, those skilled in the art will perceive improvements, changes and modifications. Such improvements, changes and modifications within the skill of the art are intended to be covered by the appended claims.

Having described specific preferred embodiments of the invention, the following is claimed:

1. An apparatus for effecting relative movement between first and second body portions interconnected by a joint, said apparatus comprising a one-piece member having a first section for engaging the first body portion, a second section for engaging the second body portion and a connector section integrally formed as one-piece with said first and second sections, a first cuff for connecting said first section of said one-piece member with the first body portion, a second cuff for connecting said second section of said one-piece member with the second body portion, and actuator means for moving said first section of said one-piece member relative to said second section of said one-piece member and flexing said connector section of said one-piece member to move said first cuff relative to said second cuff and bend the joint, said actuator means includes flexible force transmitting means connected with at least one of said sections of said one-piece member and drive means for applying force to said flexible force transmitting means to move said first and second cuffs relative to each other.

2. An apparatus as set forth in claim 1 wherein said first section of said one-piece member extends longitudinally along the first body portion and has an arcuate cross sectional configuration as viewed in a plane extending perpendicular to a longitudinal central axis of said first section of said one-piece member, said arcuate cross section of said first section of said one-piece member having a center of curvature which is disposed within a spatial envelope occupied by the first body portion when said first section of said one-piece member is connected with the first body portion.

3. An apparatus as set forth in claim 2 wherein said second section of said one-piece member extends longitudinally along the second body portion and has an arcuate cross sectional configuration as viewed in a plane extending perpendicular to a longitudinal central axis of said second section of said one-piece member, said arcuate cross section of said second section of said one-piece member having a center of curvature which is disposed within a spatial envelope occupied by the second body portion when said second section of said one-piece member is connected with the second body portion.

4. An apparatus as set forth in claim 2 wherein said connector section of said one-piece member has a longitudinal central axis which is a continuation of the longitudinal central axes of said first and second sections of said one-piece member, said connector section of said one-piece member having an arcuate cross sectional configuration as viewed in a plane extending perpendicular to the longitudinal central axis of said connector section, said arcuate cross section of said connector section of said one-piece member having a center of curvature which is disposed within a spatial envelope occupied by the joint when said first section of said one-piece member is connected with the first body portion and said second section of said one-piece member is connected with the second body portion.

5. An apparatus for effecting relative movement between first and second body portions interconnected by a joint, said apparatus comprising a one-piece member having a first section for engaging the first body portion, a second section for engaging the second body portion and a connector section integrally formed as one-piece with said first and second sections, a first cuff for connecting said first section of said one-piece member with the first body portion, a second cuff for connecting said second section of said one-piece member with the second body portion, and actuator means for moving said first section of said one-piece member relative to said second section of said one-piece member and flexing said connector section of said one-piece member to move said first cuff relative to said second cuff and bend the joint, said actuator means includes means for simultaneously applying force to end portions of said first and second sections of said one-piece member urging said first and second sections of said one-piece member to pivot in opposite directions relative to each other about said connector section of said one-piece member.

6. An apparatus as set forth in claim 5 wherein said connector section of said one-piece member has an arcuate cross sectional configuration with a center of curvature which is offset from said connector section in a direction toward the joint.

7. An apparatus as set forth in claim 5 wherein the joint has an extensor side which increases in angle as the joint is bent in flexion, said connector section of said one-piece member having a major side surface which extends along the extensor side of the joint.

8. An apparatus as set forth in claim 5 wherein the first and second body portions and the joint have an extensor side which increases in angle as the joint is bent in flexion, said one-piece member being formed as a longitudinally extending strip having first and second major side surfaces, said first major side of said longitudinally extending strip being disposed in engagement with an extensor side of said first body portion and with an extensor side of said second body portion when said first section of said one-piece member engages the first body portion and said second section of said one-piece member engages the second body portion.

9. An apparatus as set forth in claim 5 wherein the first and second body portions and the joint have an extensor side which increases in angle as the joint is bent in flexion, said one-piece member having a side surface which at least partially defines a continuous trough in which extensor side portions of the first and second body portions and the joint are received, said trough being deformable away from a linear configuration toward non-linear configuration upon flexion of the joint and being deformable away from a non-linear configuration toward a linear configuration upon extension of the joint.

10. An apparatus as set forth in claim 5 wherein the joint and first and second body portions define on one side of the joint an inner sector which decreases in angle as the joint is flexed and define on the opposite side of the joint an outer sector which decreases in angle as the joint is extended, said one-piece member being disposed in the outer sector when said first section of said one-piece member engages the first body portion and said second section of said one-piece member engages the second body portion.

11. An apparatus as set forth in claim 5 wherein said first and second cuffs include strap portions which are integrally formed as part of said one-piece member.

12. An apparatus as set forth in claim 5 wherein said connector section of said one-piece member has a smaller extent in a direction perpendicular to a longitudinal central axis of said one-piece member than said first and second sections of said one-piece member to facilitate flexing said one-piece member.

13. An apparatus as set forth in claim 5 wherein said first section of said one-piece member extends longitudinally along the first body portion and has an arcuate cross sectional configuration as viewed in a plane extending perpendicular to a longitudinal central axis of said first section of said one-piece member, said arcuate cross section of said first section of said one-piece member having a center of curvature which is disposed within a spatial envelope occupied by the first body portion when said first section of said one-piece member is connected with the first body portion.

14. An apparatus as set forth in claim 13 wherein said second section of said one-piece member extends longitudinally along the second body portion and has an arcuate cross sectional configuration as viewed in a plane extending perpendicular to a longitudinal central axis of said second section of said one-piece member, said arcuate cross section of said second section of said one-piece member having a center of curvature which is disposed within a spatial envelope occupied by the second body portion when said second section of said one-piece member is connected with the second body portion.

15. An apparatus as set forth in claim 14 wherein said connector section of said one-piece member has a longitudinal central axis which is a continuation of the longitudinal central axes of said first and second sections of said one-piece member, said connector section of said one-piece member having an arcuate cross sectional configuration as viewed in a plane extending perpendicular to the longitudinal central axis of said connector section, said arcuate cross section of said connector section of said one-piece member having a center of curvature which is disposed within a spatial envelope occupied by the joint when said first section of said one-piece member is connected with the first body portion and said second section of said one-piece member is connected with the second body portion.

16. An apparatus for effecting relative movement between first and second body portions interconnected by a joint, said apparatus comprising a one-piece member having a first section for engaging the first body portion, a second section for engaging the second body portion and a connector section integrally formed as one-piece with said first and second sections, a first cuff for connecting said first section of said one-piece member with the first body portion, a second cuff for connecting said second section of said one-piece member with the second body portion, and actuator means for moving said first section of said one-piece member relative to said second section of said one-piece member and flexing said connector section of said one-piece member to move said first cuff relative to said second cuff and bend the joint, said actuator means includes force transmitting means connected with at least one of said first and second sections of said one-piece member and drive means for placing said force transmitting means in tension to move said first and second sections of said one-piece member relative to each other.

17. An apparatus as set forth in claim 16 wherein said first section of said one-piece member extends longitudinally along the first body portion and has an arcuate cross sectional configuration as viewed in a plane extending perpendicular to a longitudinal central axis of said first section of said one-piece member, said arcuate cross section of said first section of said one-piece member having a center of curvature which is disposed within a spatial envelope occupied by the first body portion when said first section of said one-piece member is connected with the first body portion.

18. An apparatus as set forth in claim 17 wherein said second section of said one-piece member extends longitudinally along the second body portion and has an arcuate cross sectional configuration as viewed in a plane extending perpendicular to a longitudinal central axis of said second section of said one-piece member, said arcuate cross section of said second section of said one-piece member having a center of curvature which is disposed within a spatial envelope occupied by the second body portion when said second section of said one-piece member is connected with the second body portion.

19. An apparatus as set forth in claim 18 wherein said connector section of said one-piece member has a longitudinal central axis which is a continuation of the longitudinal central axes of said first and second sections of said one-piece member, said connector section of said one-piece member having an arcuate cross sectional configuration as viewed in a plane extending perpendicular to the longitudinal central axis of said connector section, said arcuate cross section of said connector section of said one-piece member having a center of curvature which is disposed within a spatial envelope occupied by the joint when said first section of said one-piece member is connected with the first body portion and said second section of said one-piece member is connected with the second body portion.

20. An apparatus as set forth in claim 16 wherein said force transmitting means includes a flexible force transmitting member connected with at least one of said sections of said one-piece member, said drive means being operable to apply force to said flexible force transmitting member to tension said flexible force transmitting member.

21. An apparatus as set forth in claim 16 wherein said force transmitting means includes means for simultaneously applying force to end portions of said first and second sections of said one-piece member urging said first and second sections of said one-piece member to pivot in opposite directions relative to each other about said connector section of said one-piece member.

22. An apparatus for effecting relative movement between first and second body portions interconnected by a joint, the joint and the first and second body portions defining on one side of the joint an inner sector which decreases in angle as the joint is flexed and on the opposite side of the joint an outer sector which decreases in angle as the joint is extended, said apparatus comprising a one-piece member having a first section for engaging the first body portion, a second section for engaging the second body portion and a connector section integrally formed as one-piece with said first and second sections, said connector section of said one-piece member being disposed in the outer sector and being offset from an axis about which at least one of the first and second body portions is pivoted upon flexion and extension of the joint, a first cuff for connecting said first section of said one-piece member with the first body portion, a second cuff for connecting said second section of said one-piece member with the second body portion, and actuator means for moving said first section of said one-piece member relative to said second section of said one-piece member and flexing said connector section of said one-piece member to move said first cuff relative to said second cuff and bend the joint.

23. An apparatus as set forth in claim 22 wherein said first section of said one-piece member extends longitudinally along the first body portion and has an arcuate cross sectional configuration as viewed in a plane extending perpendicular to a longitudinal central axis of said first section of said one-piece member, said arcuate cross section of said first section of said one-piece member having a center of curvature which is disposed within a spatial envelope occupied by the first body portion when said first section of said one-piece member is connected with the first body portion.

24. An apparatus as set forth in claim 23 wherein said second section of said one-piece member extends longitudinally along the second body portion and has an arcuate cross sectional configuration as viewed in a plane extending perpendicular to a longitudinal central axis of said second section of said one-piece member, said arcuate cross section of said second section of said one-piece member having a center of curvature which is disposed within a spatial envelope occupied by the second body portion when said second section of said one-piece member is connected with the second body portion.

25. An apparatus as set forth in claim 22 wherein said connector section of said one-piece member has a longitudinal central axis which is a continuation of longitudinal central axes of said first and second sections of said one-piece member, said connector section of said one-piece member having an arcuate cross sectional configuration as viewed in a plane extending perpendicular to the longitudinal central axis of said connector section, said arcuate cross section of said connector section of said one-piece member having a center of curvature which is disposed within a spatial envelope occupied by the joint when said first section of said one-piece member is connected with the first body portion and said second section of said one-piece member is connected with the second body portion.

26. An apparatus as set forth in claim 22 wherein said connector section of said one-piece member has an arcuate cross sectional configuration in a plane extending perpendicular to a longitudinal central axis of said one-piece member and a center of curvature which is offset from said connector section in a direction toward the joint.

27. An apparatus as set forth in claim 22 wherein the first and second body portions and the joint have an extensor side which increases in angle as the joint is bent in flexion, said one-piece member having a side surface which at least partially defines a continuous trough in which extensor side portions of the first and second body portions and the joint are received, said trough being deformable away from a linear configuration toward non-linear configuration upon flexion of the joint and being deformable away from a non-linear configuration toward a linear configuration upon extension of the joint.

28. An apparatus as set forth in claim 22 wherein the joint and first and second body portions define on one side of the joint an inner sector which decreases in angle as the joint is flexed and define on the opposite side of the joint an outer sector which decreases in angle as the joint is extended, said one-piece member being disposed in the outer sector when said first section of said one-piece member engages the first body portion and said second section of said one-piece member engages the second body portion.

29. An apparatus as set forth in claim 22 wherein said actuator means includes flexible force transmitting means connected with at least one of said sections of said one-piece member and drive means for applying force to said flexible force transmitting means to move said first and second cuffs relative to each other.

30. An apparatus as set forth in claim 22 wherein said actuator means includes means for simultaneously applying force to end portions of said first and second sections of said one-piece member urging said first and second sections of said one-piece member to pivot in opposite directions relative to each other about said connector section of said one-piece member.

31. An apparatus as set forth in claim 22 wherein said actuator means includes force transmitting means connected with at least one of said first and second sections of said one-piece member and drive means for placing said force transmitting means in tension to move said first and second sections of said one-piece member relative to each other.

32. An apparatus as set forth in claim 22 wherein said first and second cuffs include strap portions which are integrally formed as part of said one-piece member.

33. An apparatus as set forth in claim 22 wherein said actuator means includes a tower which is disposed in the outer sector and is connected with said one-piece member, said tower including surface means for defining a channel, said actuator means further includes a flexible force transmitting member which is connected with said one-piece member and extends along said channel in said tower.

34. An apparatus as set forth in claim 22 further including at least one groove formed in said connector section of said one-piece member to facilitate flexing of said connector section of said one-piece member by said actuator means.

35. An apparatus as set forth in claim 22 wherein said actuator means includes means mounted on said first section of said one-piece member for tensioning a force transmitting member connected with said second section of said one-piece member to move said second section of said one-piece member relative to said first section of said one-piece member.

36. An apparatus as set forth in claim 22 wherein said connector section of said one-piece member has a smaller extent in a direction perpendicular to a longitudinal central axis of said one-piece member than said first and second sections of said one-piece member to facilitate flexing said one-piece member.

37. An apparatus for effecting relative movement between first and second body portions interconnected by a joint, the joint and the first and second body portions defining on one side of the joint an inner sector which decreases in angle as the joint is flexed and on the opposite side of the joint an outer sector which decreases in angle as the joint is extended, said apparatus comprising a one-piece member having a first section for engaging the first body portion, a second section for engaging the second body portion and a connector section integrally formed as one-piece with said first and second sections, a first cuff for connecting said first section of said one-piece member with the first body portion, a second cuff for connecting said second section of said one-piece member with the second body portion, and actuator means for moving said first section of said one-piece member relative to said second section of said one-piece member and flexing said connector section of said one-piece member to move said first cuff relative to said second cuff and bend the joint, said one-piece member being disposed in the outer sector to effect distraction of the joint upon extension of the joint.

38. An apparatus as set forth in claim 37 wherein said connector section of said one-piece member has an arcuate cross sectional configuration with a center of curvature which is offset from said connector section in a direction toward the joint.

39. An apparatus as set forth in claim 37 wherein said first section of said one-piece member extends longitudinally along the first body portion and has an arcuate cross sectional configuration as viewed in a plane extending perpendicular to a longitudinal central axis of said first section of said one-piece member, said arcuate cross section of said first section of said one-piece member having a center of curvature which is disposed within a spatial envelope occupied by the first body portion when said first section of said one-piece member is connected with the first body portion.

40. An apparatus as set forth in claim 39 wherein said second section of said one-piece member extends longitudinally along the second body portion and has an arcuate cross sectional configuration as viewed in a plane extending perpendicular to a longitudinal central axis of said second section of said one-piece member, said arcuate cross section of said second section of said one-piece member having a center of curvature which is disposed within a spatial envelope occupied by the second body portion when said second section of said one-piece member is connected with the second body portion.

41. An apparatus as set forth in claim 37 wherein said connector section of said one-piece member has a longitudinal central axis which is a continuation of longitudinal central axes of said first and second sections of said one-piece member, said connector section of said one-piece member having an arcuate cross sectional configuration as viewed in a plane extending perpendicular to the longitudinal central axis of said connector section, said arcuate cross section of said connector section of said one-piece member having a center of curvature which is disposed within a spatial envelope occupied by the joint when said first section of said one-piece member is connected with the first body portion and said second section of said one-piece member is connected with the second body portion.

42. An apparatus as set forth in claim 37 further including at least one groove formed in said connector section of said one-piece member to facilitate flexing of said connector section of said one-piece member by said actuator means.

43. An apparatus as set forth in claim 37 wherein said actuator means includes means mounted on said first section of said one-piece member for tensioning a force transmitting member connected with said second section of said one-piece member to move said second section of said one-piece member relative to said first section of said one-piece member.

44. An apparatus as set forth in claim 37 wherein said connector section of said one-piece member has a smaller extent in a direction perpendicular to a longitudinal central axis of said one-piece member than said first and second sections of said one-piece member to facilitate flexing said one-piece member.

45. An apparatus as set forth in claim 37 wherein the first and second body portions and the joint have an extensor side which increases in angle as the joint is bent in flexion, said one-piece member having a side surface which at least partially defines a continuous trough in which extensor side portions of the first and second body portions and the joint are received, said trough being deformable away from a linear configuration toward non-linear configuration upon flexion of the joint and being deformable away from a non-linear configuration toward a linear configuration upon extension of the joint.

46. An apparatus as set forth in claim 37 wherein said actuator means includes flexible force transmitting means connected with at least one of said sections of said one-piece member and drive means for applying force to said flexible force transmitting means to move said first and second cuffs relative to each other.

47. An apparatus as set forth in claim 37 wherein said actuator means includes means for simultaneously applying force to end portions of said first and second sections of said one-piece member urging said first and second sections of said one-piece member to pivot in opposite directions relative to each other about said connector section of said one-piece member.

48. An apparatus as set forth in claim 37 wherein said actuator means includes force transmitting means connected with at least one of said first and second sections of said one-piece member and drive means for placing said force transmitting means in tension to move said first and second sections of said one-piece member relative to each other.

49. An apparatus for effecting relative movement between first and second body portions interconnected by a joint with the joint and the first and second body portions defining on one side of the joint an inner sector which decreases in angle as the joint is flexed and on the opposite side of the joint an outer sector which decreases in angle as the joint is extended, said apparatus comprising a one-piece member having a first section for engaging the first body portion, said one-piece member being disposed in the outer sector, a second section for engaging the second body portion and a connector section integrally formed as one-piece with said first and second sections, a first cuff for connecting said first section of said one-piece member with the first body portion, a second cuff for connecting said second section of said one-piece member with the second body portion, and actuator means for moving said first section of said one-piece member relative to said second section of said one-piece member and flexing said connector section of said one-piece member to move said first cuff relative to said second cuff and bend the joint, said actuator means including a tower which is disposed in the outer sector and is connected with said one-piece member, said tower including surface means for defining a channel in said tower, said actuator means further includes a flexible force transmitting member which is connected with said one-piece member and extends along said channel in said tower.

50. An apparatus as set forth in claim 49 further including at least one groove formed in said connector section of said one-piece member to facilitate flexing of said connector section of said one-piece member by said actuator means.

51. An apparatus as set forth in claim 49 wherein said connector section of said one-piece member has a smaller extent in a direction perpendicular to a longitudinal central axis of said one-piece member than said first and second sections of said one-piece member to facilitate flexing said one-piece member.

52. An apparatus as set forth in claim 49 wherein said first section of said one-piece member extends longitudinally along the first body portion and has an arcuate cross sectional configuration as viewed in a plane extending perpendicular to a longitudinal central axis of said first section of said one-piece member, said arcuate cross section of said first section of said one-piece member having a center of curvature which is disposed within a spatial envelope occupied by the first body portion when said first section of said one-piece member is connected with the first body portion.

53. An apparatus as set forth in claim 49 wherein said second section of said one-piece member extends longitudinally along the second body portion and has an arcuate cross sectional configuration as viewed in a plane extending perpendicular to a longitudinal central axis of said second section of said one-piece member, said arcuate cross section of said second section of said one-piece member having a center of curvature which is disposed within a spatial envelope occupied by the second body portion when said second section of said one-piece member is connected with the second body portion.

54. An apparatus as set forth in claim 49 wherein said connector section of said one-piece member has a longitudinal central axis which is a continuation of longitudinal central axes of said first and second sections of said one-piece member, said connector section of said one-piece member having an arcuate cross sectional configuration as viewed in a plane extending perpendicular to the longitudinal central axis of said connector section, said arcuate cross section of said connector section of said one-piece member having a center of curvature which is disposed within a spatial envelope occupied by the joint when said first section of said one-piece member is connected with the first body portion and said second section of said one-piece member is connected with the second body portion.

55. An apparatus for effecting relative movement between first and second body portions interconnected by a joint, said apparatus comprising a one-piece member having a first section for engaging the first body portion, a second section for engaging the second body portion and a connector section integrally formed as one-piece with said first and second sections, a first cuff for connecting said first section of said one-piece member with the first body portion, a second cuff for connecting said second section of said one-piece member with the second body portion, and actuator means for moving said first section of said one-piece member relative to said second section of said one-piece member and flexing said connector section of said one-piece member to move said first cuff relative to said second cuff and bend the joint, at least one groove being formed in said connector section of said one-piece member to facilitate flexing of said connector section of said one-piece member by said actuator means.

56. An apparatus as set forth in claim 55 wherein said connector section of said one-piece member has an arcuate cross sectional configuration with a center of curvature which is offset from said connector section in a direction toward the joint.

57. An apparatus as set forth in claim 55 wherein said actuator means includes means mounted on said first section of said one-piece member for tensioning a force transmitting member connected with said second section of said one-piece member to move said second section of said one-piece member relative to said first section of said one-piece member.

58. An apparatus as set forth in claim 55 wherein said connector section of said one-piece member has a smaller extent in a direction perpendicular to a longitudinal central axis of said one-piece member than said first and second sections of said one-piece member to facilitate flexing said one-piece member.

59. An apparatus as set forth in claim 55 wherein said first section of said one-piece member extends longitudinally along the first body portion and has an arcuate cross sectional configuration as viewed in a plane extending perpendicular to a longitudinal central axis of said first section of said one-piece member, said arcuate cross section of said first section of said one-piece member having a center of curvature which is disposed within a spatial envelope occupied by the first body portion when said first section of said one-piece member is connected with the first body portion.

60. An apparatus as set forth in claim 59 wherein said second section of said one-piece member extends longitudinally along the second body portion and has an arcuate cross sectional configuration as viewed in a plane extending perpendicular to a longitudinal central axis of said second section of said one-piece member, said arcuate cross section of said second section of said one-piece member having a center of curvature which is disposed within a spatial envelope occupied by the second body portion when said second section of said one-piece member is connected with the second body portion.

61. An apparatus as set forth in claim 55 wherein said connector section of said one-piece member has a longitudinal central axis which is a continuation of longitudinal central axes of said first and second sections of said one-piece member, said connector section of said one-piece member having an arcuate cross sectional configuration as viewed in a plane extending perpendicular to the longitudinal central axis of said connector section, said arcuate cross section of said connector section of said one-piece member having a center of curvature which is disposed within a spatial envelope occupied by the joint when said first section of said one-piece member is connected with the first body portion and said second section of said one-piece member is connected with the second body portion.

62. An apparatus as set forth in claim 55 wherein the first and second body portions and the joint have an extensor side which increases in angle as the joint is bent in flexion, said one-piece member having a side surface which at least partially defines a continuous trough in which extensor side portions of the first and second body portions and the joint are received, said trough being deformable away from a linear configuration toward non-linear configuration upon flexion of the joint and being deformable away from a non-linear configuration toward a linear configuration upon extension of the joint.

63. An apparatus as set forth in claim 55 wherein the joint and first and second body portions define on one side of the joint an inner sector which decreases in angle as the joint is flexed and define on the opposite side of the joint an outer sector which decreases in angle as the joint is extended, said one-piece member being disposed in the outer sector when said first section of said one-piece member engages the first body portion and said second section of said one-piece member engages the second body portion.

64. An apparatus as set forth in claim 55 wherein said actuator means includes flexible force transmitting means connected with at least one of said sections of said one-piece member and drive means for applying force to said flexible force transmitting means to move said first and second cuffs relative to each other.

65. An apparatus as set forth in claim 55 wherein said actuator means includes means for simultaneously applying force to end portions of said first and second sections of said one-piece member urging said first and second sections of said one-piece member to pivot in opposite directions relative to each other about said connector section of said one-piece member.

66. An apparatus as set forth in claim 55 wherein said actuator means includes force transmitting means connected with at least one of said first and second sections of said one-piece member and drive means for placing said force transmitting means in tension to move said first and second sections of said one-piece member relative to each other.

67. An apparatus as set forth in claim 55 wherein said first and second cuffs include strap portions which are integrally formed as part of said one-piece member.

68. An apparatus as set forth in claim 55 wherein said actuator means includes means mounted on said first section of said one-piece member for tensioning a force transmitting member connected with said second section of said one-piece member to move said second section of said one-piece member relative to said first section of said one-piece member.

69. An apparatus as set forth in claim 55 wherein said connector section of said one-piece member has a smaller extent in a direction perpendicular to a longitudinal central axis of said one-piece member than said first and second sections of said one-piece member to facilitate flexing said one-piece member.

70. An apparatus for effecting relative movement between first and second body portions interconnected by a joint, said apparatus comprising a one-piece member having a first section for engaging the first body portion, a second section for engaging the second body portion and a connector section integrally formed as one-piece with said first and second sections, a first cuff for connecting said first section of said one-piece member with the first body portion, a second cuff for connecting said second section of said one-piece member with the second body portion, and actuator means for moving said first section of said one-piece member relative to said second section of said one-piece member and flexing said connector section of said one-piece member to move said first cuff relative to said second cuff and bend the joint, said actuator means includes means mounted on said first section of said one-piece member for tensioning a force transmitting member connected with said second section of said one-piece member to move said second section of said one-piece member relative to said first section of said one-piece member.

71. An apparatus as set forth in claim 70 wherein said connector section of said one-piece member has an arcuate cross sectional configuration with a center of curvature which is offset from said connector section in a direction toward the joint.

72. An apparatus as set forth in claim 70 further including at least one groove formed in said connector section of said one-piece member to facilitate flexing of said connector section of said one-piece member by said actuator means.

73. An apparatus as set forth in claim 70 wherein said connector section of said one-piece member has a smaller extent in a direction perpendicular to a longitudinal central axis of said one-piece member than said first and second sections of said one-piece member to facilitate flexing said one-piece member.

74. An apparatus as set forth in claim 73 wherein said first section of said one-piece member extends longitudinally along the first body portion and has an arcuate cross sectional configuration as viewed in a plane extending perpendicular to a longitudinal central axis of said first section of said one-piece member, said arcuate cross section of said first section of said one-piece member having a center of curvature which is disposed within a spatial envelope occupied by the first body portion when said first section of said one-piece member is connected with the first body portion.

75. An apparatus as set forth in claim 74 wherein said second section of said one-piece member extends longitudinally along the second body portion and has an arcuate cross sectional configuration as viewed in a plane extending perpendicular to a longitudinal central axis of said second section of said one-piece member, said arcuate cross section of said second section of said one-piece member having a center of curvature which is disposed within a spatial envelope occupied by the second body portion when said second section of said one-piece member is connected with the second body portion.

76. An apparatus as set forth in claim 70 wherein said connector section of said one-piece member has a longitudinal central axis which is a continuation of longitudinal central axes of said first and second sections of said one-piece member, said connector section of said one-piece member having an arcuate cross sectional configuration as viewed in a plane extending perpendicular to the longitudinal central axis of said connector section, said arcuate cross section of said connector section of said one-piece member having a center of curvature which is disposed within a spatial envelope occupied by the joint when said first section of said one-piece member is connected with the first body portion and said second section of said one-piece member is connected with the second body portion.

77. An apparatus as set forth in claim 70 wherein the joint has an extensor side which increases in angle as the joint is bent in flexion, said connector section of said one-piece member having a major side surface which extends along the extensor side of the joint.

78. An apparatus as set forth in claim 70 wherein the first and second body portions and the joint have an extensor side which increases in angle as the joint is bent in flexion, said one-piece member being formed as a longitudinally extending strip having first and second major side surfaces, said first major side of said longitudinally extending strip being disposed in engagement with an extensor side of said first body portion and with an extensor side of said second body portion when said first section of said one-piece member engages the first body portion and said second section of said one-piece member engages the second body portion.

79. An apparatus as set forth in claim 70 wherein the first and second body portions and the joint have an extensor side which increases in angle as the joint is bent in flexion, said one-piece member having a side surface which at least partially defines a continuous trough in which extensor side portions of the first and second body portions and the joint are received, said trough being deformable away from a linear configuration toward non-linear configuration upon flexion of the joint and being deformable away from a non-linear configuration toward a linear configuration upon extension of the joint.

80. An apparatus as set forth in claim 70 wherein the joint and first and second body portions define on one side of the joint an inner sector which decreases in angle as the joint is flexed and define on the opposite side of the joint an outer sector which decreases in angle as the joint is extended, said one-piece member being disposed in the outer sector when said first section of said one-piece member engages the first body portion and said second section of said one-piece member engages the second body portion.

81. An apparatus for effecting relative movement between first and second body portions interconnected by a joint, the first and second body portions and the joint having flexor and extensor sides, said apparatus comprising a first section for engaging the extensor side of the first body portion, a second section for engaging the extensor side of the second body portion, a first cuff for connecting said first section with the first body portion, a second cuff for connecting said second section with the second body portion, a flexible connector section extending between said first and second sections, said flexible connector section extending along the extensor side of the joint when said first and second sections are connected with the first and second body portions, and actuator means for flexing said connector section and moving said first section relative to said second section to bend the joint, said actuator means includes a tower which is connected with said first section, said tower including surface means for defining a channel in said tower, said actuator means further includes a flexible force transmitting member which is connected with said first and second sections and extends along said channel in said tower and means connected with said flexible force transmitting member to tension said flexible force transmitting member.

82. An apparatus as set forth in claim 81 wherein said flexible connector section is formed by a single piece of material having an arcuate cross sectional configuration as viewed in a plane extending perpendicular to said first and second sections when the joint is in an extended condition.

83. An apparatus as set forth in claim 81 wherein said flexible connector section has a first end portion connected with one end of said first section and a second end portion connected with one end of said second section, said one end of said first section being spaced a first distance from said one end of said second section when said first and second sections are connected with the first and second body portions and the joint is in an extended condition, said one end of said first section being spaced a second distance from said one end of said second section when said first and second sections are connected with the first and second body portions and the joint is in a flexed condition, said second distance being greater than said first distance.

84. An apparatus as set forth in claim 81 wherein said first cuff includes a first cuff strap which is integrally formed as one-piece with said first section, said second cuff including a second cuff strap which is integrally formed as one-piece with said second section.

85. An apparatus as set forth in claim 81 further including at lest one groove formed in said connector section and extending across said connector section in a direction transverse to a longitudinal central axis of said connector section to facilitate flexing of said connector section by said actuator means.

86. An apparatus as set forth in claim 81 wherein said first section extends longitudinally along the first body portion and has an arcuate cross sectional configuration as viewed in a plane extending perpendicular to a longitudinal central axis of said first section, said arcuate cross section of said first section having a center of curvature which is disposed within a spatial envelope occupied by the first body portion when said first section is connected with the first body portion.

87. An apparatus as set forth in claim 86 wherein said second section extends longitudinally along the second body portion and has an arcuate cross sectional configuration as viewed in a plane extending perpendicular to a longitudinal central axis of said second section, said arcuate cross section of said second section having a center of curvature which is disposed within a spatial envelope occupied by the second body portion when said second section is connected with the second body portion.

88. An apparatus as set forth in claim 81 wherein said connector section has a longitudinal central axis which is aligned with longitudinal central axes of said first and second sections, said connector section having an arcuate cross sectional configuration as viewed in a plane extending perpendicular to the central axis of said connector section, said arcuate cross section of said connector section having a center of curvature which is disposed within a spatial envelope occupied by the joint when said first section is connected with the first body portion and said second section is connected with the second body portion.

89. An apparatus as set forth in claim 81 wherein said first section, second section and connector section are integrally formed as one piece.

90. An apparatus for effecting relative movement between first and second body portions interconnected by a joint, the first and second body portions and the joint having flexor and extensor sides, said apparatus comprising a first section for engaging the extensor side of the first body portion, a second section for engaging the extensor side of the second body portion, a first cuff for connecting said first section with the first body portion, a second cuff for connecting said second section with the second body portion, a flexible connector section extending between said first and second sections, said flexible connector section extending along the extensor side of the joint when said first and second sections are connected with the first and second body portions, and actuator means for flexing said connector section and moving said first section relative to said second section to bend the joint, at least one groove formed in said connector section and extending across said connector section in a direction transverse to a longitudinal central axis of said connector section to facilitate flexing of said connector section by said actuator means.

91. An apparatus as set forth in claim 90 wherein said flexible connector section is formed by a single piece of material having an arcuate cross sectional configuration as viewed in a plane extending perpendicular to said first and second sections when the joint is in an extended condition.

92. An apparatus as set forth in claim 90 wherein said flexible connector section has a first end portion connected with one end of said first section and a second end portion connected with one end of said second section, said one end of said first section being spaced a first distance from said one end of said second section when said first and second sections are connected with the first and second body portions and the joint is in an extended condition, said one end of said first section being spaced a second distance from said one end of said second section when said first and second sections are connected with the first and second body portions and the joint is in a flexed condition, said second distance being greater than said first distance.

93. An apparatus as set forth in claim 90 wherein said first cuff includes a first cuff strap which is integrally formed as one-piece with said first section, said second cuff including a second cuff strap which is integrally formed as one-piece with said second section.

94. An apparatus as set forth in claim 90 wherein said actuator means includes means mounted on said first section for tensioning a force transmitting member connected with said second section to move said second section relative to said first section.

95. An apparatus as set forth in claim 90 wherein said first section extends longitudinally along the first body portion and has an arcuate cross sectional configuration as viewed in a plane extending perpendicular to a longitudinal central axis of said first section, said arcuate cross section of said first section having a center of curvature which is disposed within a spatial envelope occupied by the first body portion when said first section is connected with the first body portion.

96. An apparatus as set forth in claim 94 wherein said second section extends longitudinally along the second body portion and has an arcuate cross sectional configuration as viewed in a plane extending perpendicular to a longitudinal central axis of said second section, said arcuate cross section of said second section having a center of curvature which is disposed within a spatial envelope occupied by the second body portion when said second section is connected with the second body portion.

97. An apparatus as set forth in claim 90 wherein said connector section has a longitudinal central axis which is aligned with longitudinal central axes of said first and second sections, said connector section having an arcuate cross sectional configuration as viewed in a plane extending perpendicular to the central axis of said connector section, said arcuate cross section of said connector section having a center of curvature which is disposed within a spatial envelope occupied by the joint when said first section is connected with the first body portion and said second section is connected with the second body portion.

98. An apparatus as set forth in claim 90 wherein said first section, second section and connector section are integrally formed as one piece.

99. An apparatus for effecting relative movement between first and second body portions interconnected by a joint, the first and second body portions and the joint having flexor and extensor sides, said apparatus comprising a first section for engaging the extensor side of the first body portion, a second section for engaging the extensor side of the second body portion, a first cuff for connecting said first section with the first body portion, a second cuff for connecting said second section with the second body portion, a flexible connector section extending between said first and second sections, said flexible connector section extending along the extensor side of the joint when said first and second sections are connected with the first and second body portions, and actuator means for flexing said connector section and moving said first section relative to said second section to bend the joint, said actuator means includes means mounted on said first section for tensioning a force transmitting member connected with said second section to move said second section relative to said first section.

100. An apparatus as set forth in claim 99 wherein said first section extends longitudinally along the first body portion and has an arcuate cross sectional configuration as viewed in a plane extending perpendicular to a longitudinal central axis of said first section, said arcuate cross section of said first section having a center of curvature which is disposed within a spatial envelope occupied by the first body portion when said first section is connected with the first body portion.

101. An apparatus as set forth in claim 100 wherein said second section extends longitudinally along the second body portion and has an arcuate cross sectional configuration as viewed in a plane extending perpendicular to a longitudinal central axis of said second section, said arcuate cross section of said second section having a center of curvature which is disposed within a spatial envelope occupied by the second body portion when said second section is connected with the second body portion.

102. An apparatus as set forth in claim 101 wherein said connector section has a longitudinal central axis which is aligned with the longitudinal central axes of said first and second sections, said connector section having an arcuate cross sectional configuration as viewed in a plane extending perpendicular to the central axis of said connector section, said arcuate cross section of said connector section having a center of curvature which is disposed within a spatial envelope occupied by the joint when said first section is connected with the first body portion and said second section is connected with the second body portion.

103. An apparatus as set forth in claim 99 wherein said first section, second section and connector section are integrally formed as one piece.

104. An apparatus as set forth in claim 99 wherein said flexible connector section is formed by a single piece of material having an arcuate cross sectional configuration as viewed in a plane extending perpendicular to said first and second sections when the joint is in an extended condition.

105. An apparatus for effecting relative movement between first and second body sections interconnected by a joint, said apparatus comprising a first section for engaging the first body portion, a second section for engaging the second body portion, a first cuff for connecting the first section with the first body portion, a second cuff for connecting said second section with the second body portion, a flexible connector section extending between said first and second sections, and actuator means for flexing said connector section and moving said first section relative to said second section to bend the joint, said actuator means including a tower which is connected with and projects outward from said first section and a flexible force transmitting member which is connected with the first and second sections and extends along a channel in said tower.

106. An apparatus as set forth in claim 105 further including means connected with one of said first and second sections for tensioning said flexible force transmitting member to move said flexible force transmitting member along the channel formed in said tower.

107. An apparatus as set forth in claim 106 wherein said first section, said second section and said connector section are integrally formed as one piece.

108. An apparatus as set forth in claim 105 wherein the joint and first and second body portions define on one side of the joint an inner sector which decreases in angle as the joint is flexed and define on the opposite side of the joint an outer sector which decreases in angle as the joint is extended, said tower being disposed in the outer sector when said first section engages said first body portion.

109. An apparatus for effecting relative movement between first and second body portions interconnected by a joint, said apparatus comprising a first arm section for engaging the first body portion, a second arm section for engaging the second body portion, and a connector section interconnecting said first and second arm sections, a first cuff for connecting said first arm section with the first body portion, a second cuff for connecting said second arm section with the second body portion, and actuator means for flexing said connector section to move said first cuff relative to said second cuff and bend the joint, said actuator means including a flexible force transmitting member connected with said first arm section adjacent to said first cuff and a drive means connected with said second arm section adjacent to said second cuff, said drive means being operable to tension said flexible force transmitting member to transmit force from said drive means to said first arm section.

110. An apparatus as set forth in claim 109 wherein said drive means includes a manually engageable member which is rotatable relative to said second arm section to tension said flexible force transmitting member.

111. An apparatus as set forth in claim 109 further including a tower connected with said second arm section and disposed in the outer sector, said flexible force transmitting element extends from said drive means to said tower and extends from said tower to said first arm section.

112. An apparatus as set forth in claim 111 wherein said tower includes a channel along which the flexible force transmitting member extends, said channel having a longitudinal central axis which is skewed at an acute angle to a longitudinal central axis of said second arm section.

113. An apparatus as set forth in claim 109 wherein said first arm section, s aid second arm section and said connector section are integrally formed as one piece.

114. An apparatus as set forth in claim 109 wherein said first arm section extends along an extensor side of the first body portion, said second arm section extends along an extensor side of the second body portion, and said connector section extends along an extensor side of the joint.

115. An apparatus as set forth in claim 109 wherein said first arm section, said connector section and said second arm section cooperate to form a continuous trough having an arcuate cross sectional configuration and in which the first body portion, joint and second body portion are at least partially disposed.

116. An apparatus as set forth in claim 109 wherein said drive means includes a drum which is rotatably mounted on said second arm section and a handle which is connected with said drum and is manually rotatable relative to said second arm section to rotate said drum and wind said flexible force transmitting member onto said drum.

117. An apparatus as set forth in claim 116 wherein said drive means further includes a ratchet mechanism which is operable to block rotation of said drum in a direction in which said flexible force transmitting member is unwound from said drum, said ratchet mechanism including a ratchet wheel which is fixedly connected with said drum and a pawl which is engageable with said ratchet wheel.

118. An apparatus for effecting relative movement between first and second body portions interconnected by a joint, said apparatus comprising a one-piece member having a first section for engaging the first body portion, a second section integrally formed as one piece with the first section for engaging the second body portion, a connector section integrally formed as one-piece with and extending between said first and second sections, a first cuff connected with said first section for connecting said first section of said one-piece member with the first body portion, and a second cuff connected with said second section for connecting said second section of said one-piece member with the second body portion, and actuator means for applying force to said first section of said one-piece member to move said first section of said one-piece member relative to said second section of said one-piece member and to flex said connector section of said one-piece member to move said first cuff relative to said second cuff and bend the joint under the influence of force applied to said one-piece member by said actuator means.

119. An apparatus as set forth in claim 118 wherein said connector section of said one-piece member has an arcuate cross sectional configuration as viewed in a plane extending perpendicular to a longitudinal central axis of said connector section and through a center of curvature of said connector section, the center of curvature of said connector section being offset from said connector section in a direction toward the joint.

120. An apparatus as set forth in claim 118 wherein said first section of said one-piece member extends longitudinally along the first body portion and has an arcuate cross sectional configuration as viewed in a plane extending perpendicular to a longitudinal central axis of said first section of said one-piece member, said arcuate cross section of said first section of said one-piece member having a center of curvature which is disposed within a spatial envelope occupied by the first body portion when said first section of said one-piece member is connected with the first body portion, said first cuff being integrally formed as one piece with said first section of said one-piece member.

121. An apparatus as set forth in claim 120 wherein said second section of said one-piece member extends longitudinally along the second body portion and has an arcuate cross sectional configuration as viewed in a plane extending perpendicular to a longitudinal central axis of said second section of said one-piece member, said arcuate cross section of said second section of said one-piece member having a center of curvature which is disposed within a spatial envelope occupied by the second body portion when said second section of said one-piece member is connected with the second body portion, said second cuff being integrally formed as one piece with said second section of said one-piece member.

122. An apparatus as set forth in claim 118 wherein said connector section of said one-piece member has a longitudinal central axis which is a continuation of longitudinal central axes of said first and second sections of said one-piece member, said connector section of said one-piece member having an arcuate cross sectional configuration as viewed in a plane extending perpendicular to the longitudinal central axis of said connector section, said arcuate cross section of said connector section of said one-piece member having a center of curvature which is disposed within a spatial envelope occupied by the joint when said first section of said one-piece member is connected with the first body portion and said second section of said one-piece member is connected with the second body portion.

123. An apparatus as set forth in claim 118 wherein the joint has an extensor side which increases in angle as the joint is bent in flexion, said connector section of said one-piece member having a major side surface which extends along the extensor side of the joint.

124. An apparatus as set forth in claim 118 wherein the first and second body portions and the joint have an extensor side which increases in angle as the joint is bent in flexion, said one-piece member being formed as a longitudinally extending strip having first and second major side surfaces, said first major side of said longitudinally extending strip being disposed in engagement with an extensor side of said first body portion and with an extensor side of said second body portion when said first section of said one-piece member engages the first body portion and said second section of said one-piece member engages the second body portion.

125. An apparatus as set forth in claim 118 wherein the first and second body portions and the joint have an extensor side which increases in angle as the joint is bent in flexion, said one-piece member having a side surface which at least partially defines a continuous trough in which extensor side portions of the first and second body portions and the joint are received, said trough being deformable away from a linear configuration toward non-linear configuration upon flexion of the joint and being deformable away from a non-linear configuration toward a linear configuration upon extension of the joint.

126. An apparatus as set forth in claim 118 wherein the joint and first and second body portions define on one side of the joint an inner sector which decreases in angle as the joint is flexed and define on the opposite side of the joint an outer sector which decreases in angle as the joint is extended, said one-piece member being disposed in the outer sector when said first section of said one-piece member engages the first body portion and said second section of said one-piece member engages the second body portion.

127. An apparatus as set forth in claim 118 wherein said actuator means includes flexible force transmitting means connected with at least one of said sections of said one-piece member and drive means for applying force to said flexible force transmitting means to move said first and second cuffs relative to each other.

128. An apparatus as set forth in claim 118 wherein said actuator means includes means for simultaneously applying force to end portions of said first and second sections of said one-piece member urging said first and second sections of said one-piece member to pivot in opposite directions relative to each other about said connector section of said one-piece member.

129. An apparatus as set forth in claim 118 wherein said actuator means includes force transmitting means connected with at least one of said first and second sections of said one-piece member and drive means for placing said force transmitting means in tension to move said first and second sections of said one-piece member relative to each other.

130. An apparatus as set forth in claim 118 wherein the joint and the first and second body portions define on one side of the joint an inner sector which decreases in angle as the joint is flexed and defined on the opposite side of the joint an outer sector which decreases in angle as the joint is extended, said connector section of said one-piece member being disposed in the outer sector and being offset from an axis about which at least one of the first and second body portions is pivoted upon flexion and extension of the joint.

131. An apparatus as set forth in claim 118 wherein the joint and the first and second body portions define on one side of the joint an inner sector which decreases in angle as the joint is flexed and define on the opposite side an outer sector which decreases in angle as the joint is extended, said one-piece member being disposed in the outer sector to effect distraction of the joint upon extension of the joint.

132. An apparatus as set forth in claim 118 wherein said first and second cuffs include strap portions which are integrally formed as part of said one-piece member.

133. An apparatus as set forth in claim 118 wherein the joint and the first and second body portions define on one side of the joint an inner sector which decreases in angle as the joint is flexed and define on the opposite side of the joint an outer sector which decreases in angle as the joint is extended, said one-piece member being disposed in the outer sector, said actuator means including a tower which is disposed in the outer sector and is connected with said one-piece member, said actuator means further includes a force transmitting member which is connected with said one-piece member and with said tower.

134. An apparatus as set forth in claim 118 further including at least one groove formed in said connector section of said one-piece member to facilitate flexing of said connector section of said one-piece member by said actuator means.

135. An apparatus as set forth in claim 118 wherein said actuator means includes means mounted on said first section of said one-piece member for tensioning a force transmitting member connected with said second section of said one-piece member to move said second section of said one-piece member relative to said first section of said one-piece member.

136. An apparatus as set forth in claim 118 wherein said connector section of said one-piece member has a smaller extent in a direction perpendicular to a longitudinal central axis of said one-piece member than said first and second sections of said one-piece member to facilitate flexing said one-piece member.

\* \* \* \* \*

UNITED STATES PATENT AND TRADEMARK OFFICE
CERTIFICATE OF CORRECTION

PATENT NO. : 5,685,830
DATED : November 11, 1997
INVENTOR(S) : Peter M. Bonutti

It is certified that error appears in the above-indentified patent and that said Letters Patent is hereby corrected as shown below:

Column 29, line 45, change "lest" to --least--.

Column 31, line 5, change "94" to --95--.

Signed and Sealed this

Twenty-second Day of September, 1998

Attest:

BRUCE LEHMAN

Attesting Officer          Commissioner of Patents and Trademarks